United States Patent
Nedelcu

(10) Patent No.: US 10,132,916 B2
(45) Date of Patent: Nov. 20, 2018

(54) POWER SAVING INTELLIGENT LOCATOR

(71) Applicant: Intelligent Locations, LLC, North Barrington, IL (US)

(72) Inventor: Bogdan R. Nedelcu, North Barrington, IL (US)

(73) Assignee: Intelligent Locations, LLC, North Barrington, IL (US)

( * ) Notice: Subject to any disclaimer, the term of this patent is extended or adjusted under 35 U.S.C. 154(b) by 0 days.

(21) Appl. No.: 15/165,576

(22) Filed: May 26, 2016

(65) Prior Publication Data

US 2016/0350564 A1    Dec. 1, 2016

Related U.S. Application Data

(60) Provisional application No. 62/166,921, filed on May 27, 2015.

(51) Int. Cl.
| | |
|---|---|
| *H04Q 5/22* | (2006.01) |
| *G01S 5/02* | (2010.01) |
| *G01S 5/00* | (2006.01) |
| *G06Q 10/00* | (2012.01) |

(52) U.S. Cl.
CPC .......... *G01S 5/0284* (2013.01); *G01S 5/0018* (2013.01); *G06Q 10/00* (2013.01)

(58) Field of Classification Search
None
See application file for complete search history.

(56) References Cited

U.S. PATENT DOCUMENTS

| | | | |
|---|---|---|---|
| 5,900,801 A | * | 5/1999 | Heagle ............... G06Q 50/12 340/286.09 |
| 7,855,651 B2 | | 12/2010 | LeBlond et al. |
| 7,877,082 B2 | | 1/2011 | Eagle et al. |
| 8,285,564 B2 | | 10/2012 | Perkins |
| 8,294,585 B2 | | 10/2012 | Barnhill |
| 8,564,431 B2 | | 10/2013 | Snodgrass |
| 8,988,228 B2 | | 3/2015 | Iseri et al. |

(Continued)

FOREIGN PATENT DOCUMENTS

WO    2015061718 A1    4/2015

*Primary Examiner* — Adolf Dsouza
(74) *Attorney, Agent, or Firm* — Greenberg Traurig, LLP; David J. Dykeman

(57) ABSTRACT

Systems and methods of a power saving intelligent locator system for locating a user within a space, the system includes providing a tag cloud having tags that communicate tag data with aggregators. The tag cloud and aggregators located within the space form a meshed network, the aggregators communicate data to a computer in communication with a cloud-based network. A user smart device with a mobile application wirelessly communicates with an internet system in communication with the cloud-based network. Receiving by the computer, information about the user smart device entering the meshed network by wireless tags positioned within the space. Information is obtained by the tags during a recognition process by wirelessly transmitting messages between the wireless tags to aggregators, and then wirelessly transmitting information from the aggregators to the computer, the computer communicates with the cloud-based network, the wireless tags transition from a sleep state to an active state.

20 Claims, 18 Drawing Sheets

(56) References Cited

U.S. PATENT DOCUMENTS

| | | |
|---|---|---|
| 9,060,655 B2 | 6/2015 | Iseri et al. |
| 9,183,729 B2 | 11/2015 | Hines et al. |
| 2005/0250552 A1 | 11/2005 | Eagle et al. |
| 2012/0248140 A1 | 10/2012 | Iseri et al. |
| 2013/0030915 A1* | 1/2013 | Statler .................... G06Q 30/02 705/14.54 |
| 2013/0122807 A1 | 5/2013 | Tenarvitz et al. |
| 2013/0250823 A1* | 9/2013 | Gaylard ............... H04W 4/005 370/310 |
| 2013/0262034 A1 | 10/2013 | Iseri et al. |
| 2014/0229196 A1 | 8/2014 | Perkins |
| 2014/0266730 A1 | 9/2014 | Hines et al. |
| 2016/0267772 A1* | 9/2016 | Iseri .................... G08B 21/245 |

* cited by examiner

Implementation Example

- Red Dots Represent a "heat map" of consumers roaming inside the store
- We can measure the hits and duration – how long the same customer stayed in the area
- Cloud based analytics are then used to compute the gathered data Pre-requisites (SSI= Signal Strength Indicator):
1. Personnel have a Tag ID alongside their badge
2. Sanitizer pump has an accelerometer tag, able to detect variations in the z-axis vales, with x & y constant – fixed tag
3. Each sanitizer pump has a pre-calibrated value of the BT SSI value in the IL CLOUD database along with a standard deviation value
4. Agg N is the one that receives the strongest signal from Tag Z, Agg N-1 and Agg N+1 being its closest neighbors

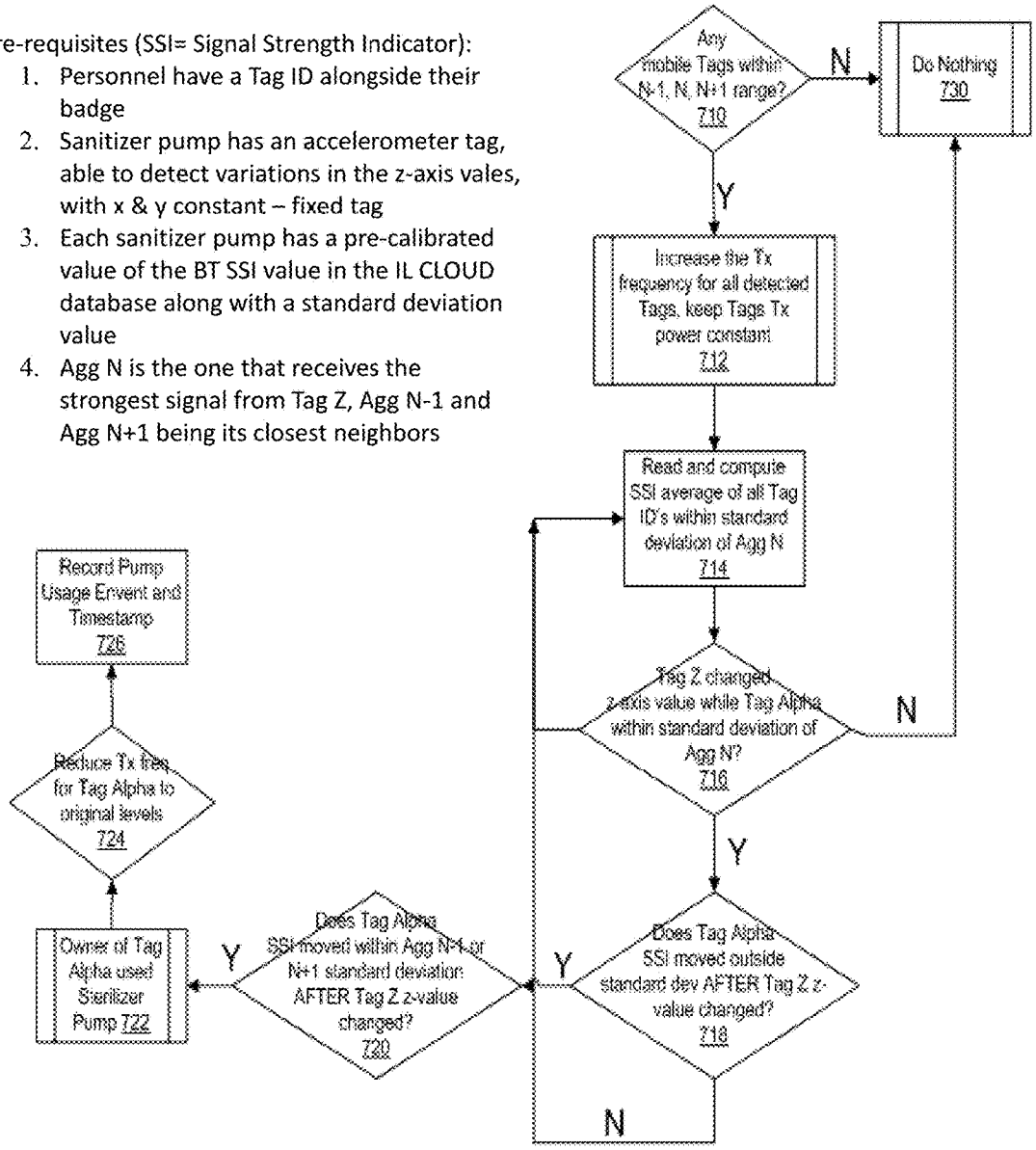

FIG. 7

POWER SAVING INTELLIGENT LOCATOR

CROSS-REFERENCE TO RELATED APPLICATIONS

This application claims the benefit of U.S. Provisional Application Ser. No. 62/166,921 titled "Power Saving Intelligent Locator", filed on May 27, 2015, which is hereby incorporated by reference in its entirety.

FIELD

The present disclosure relates to power saving intelligent locating applications and wireless communication applications, systems and methods.

BACKGROUND

There are systems employed for indoor positioning that are typically based on inertial navigation wherein these systems generally incorporate technologies such as Global Positioning System (GPS). With increasing technological advances and a consumer spending driven economy, businesses are looking to find ways to gather data to track consumer foot traffic within the retail space to increase sales other than using GPS systems. Given the recent slump in brick and mortar stores challenged by increasing on line purchases, the ability to gather information about shoppers spending habits, traffic through the stores or even being able to reduce the number of store personnel is critical to the survival of some stores, such as specialty stores.

SUMMARY

A power saving intelligent locator system for locating a user within a space, the system including providing a tag cloud having multiple tags that communicate tag data with aggregators, wherein the tag cloud and aggregators are located within the space and form a meshed network, the aggregators communicate data to a central computer that is in communication with a cloud-based network; providing a user smart device capable of downloading a mobile application wirelessly and wirelessly communicating with an internet system that is in communication with the cloud-based network; receiving by the central computer, information about the user smart device entering the meshed network by wireless tags positioned within the space; wherein the information is obtained by the wireless tags during a recognition process that comprises wirelessly transmitting messages between the wireless tags to aggregators, then wirelessly transmitting the information from the aggregators to the central computer, wherein the central computer communicates with the cloud-based network, wherein the wireless tags transition from a sleep state to an active state; determining locations of the user smart device in the space in response to the information and to calibration information indicative of an actual or estimated location of the user smart device within the space; receiving, from cloud-base network, user smart device information related to a location of the user smart device in relation to wireless tags within the space, for the user to open the mobile application on the user smart device of the user; receiving, from the user of the user smart device, user smart device information related to a location of the user smart device in relation to a sub-set of the wireless tags; determining a location of the user smart device within the space in response to the user smart device location information and to locations of the wireless tags of the sub-set of wireless tags in the space, wherein each tag of the tags not within an approximate range of the user smart device within the space, receives wireless transmissions from other tags to transition from the active state to the sleep state.

In an embodiment, a method comprises creating, by a plurality of radio emitting devices each comprising a processor and transceiver, a geo-fence within a space, each radio emitting device capable of communicating with neighboring radio emitting devices in the plurality and capable of communicating with aggregators in communication with a central server computer over a network; and determining, by a subset of the plurality of radio emitting devices, a location of a user computing device executing a user application for the space when the user computing device is moved past the geo-fence and into the space, the determined location relative to the subset of the radio emitting devices, each radio emitting device in the subset transitioning from a sleep state to an active state when the user computing device moves within a predetermined distance from the subset of the radio emitting devices.

In an embodiment, a radio emitting device comprises a processor; a transceiver for communicating with other radio emitting devices and for communicating with an aggregator in communication with a central server computer over a network; and a storage medium for tangibly storing thereon program logic for execution by the processor, the program logic comprising radio emitting device communicating logic executed by the processor for communicating with a plurality of radio emitting devices to create a geo-fence within a space and for facilitating determination of a location of a user computing device by the radio emitting device and a subset of the plurality of radio emitting devices, the user computing device executing a user application for the space, the facilitating determination of the location occurring when the user computing device is moved past the geo-fence and into the space, the determined location relative to the radio emitting device, the radio emitting device transitioning from a sleep state to an active state when the user computing device moves within a predetermined distance from the subset of the radio emitting devices.

In an embodiment, a non-transitory computer readable storage medium tangibly storing thereon computer instructions for execution by a processor of a radio emitting device, the computer instructions comprising communicating with a plurality of radio emitting devices to create a geo-fence within a space and for facilitating determination of a location of a user computing device by the radio emitting device and a subset of the plurality of radio emitting devices, the user computing device executing a user application for the space, the facilitating determination of the location occurring when the user computing device is moved past the geo-fence and into the space, the determined location relative to the radio emitting device, the radio emitting device transitioning from a sleep state to an active state when the user computing device moves within a predetermined distance from the subset of the radio emitting devices.

DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 6B is a flow diagram illustrating the steps for a store manager to gather data specific to the consumer's movement within the consumer store or warehouse, according to an embodiment of the present disclosure;

FIG. 7 is a flow diagram illustrating an algorithm used to detect the usage of the sanitizer dispenser in a meshed network, according to an embodiment of the present disclosure;

Figure 1A:
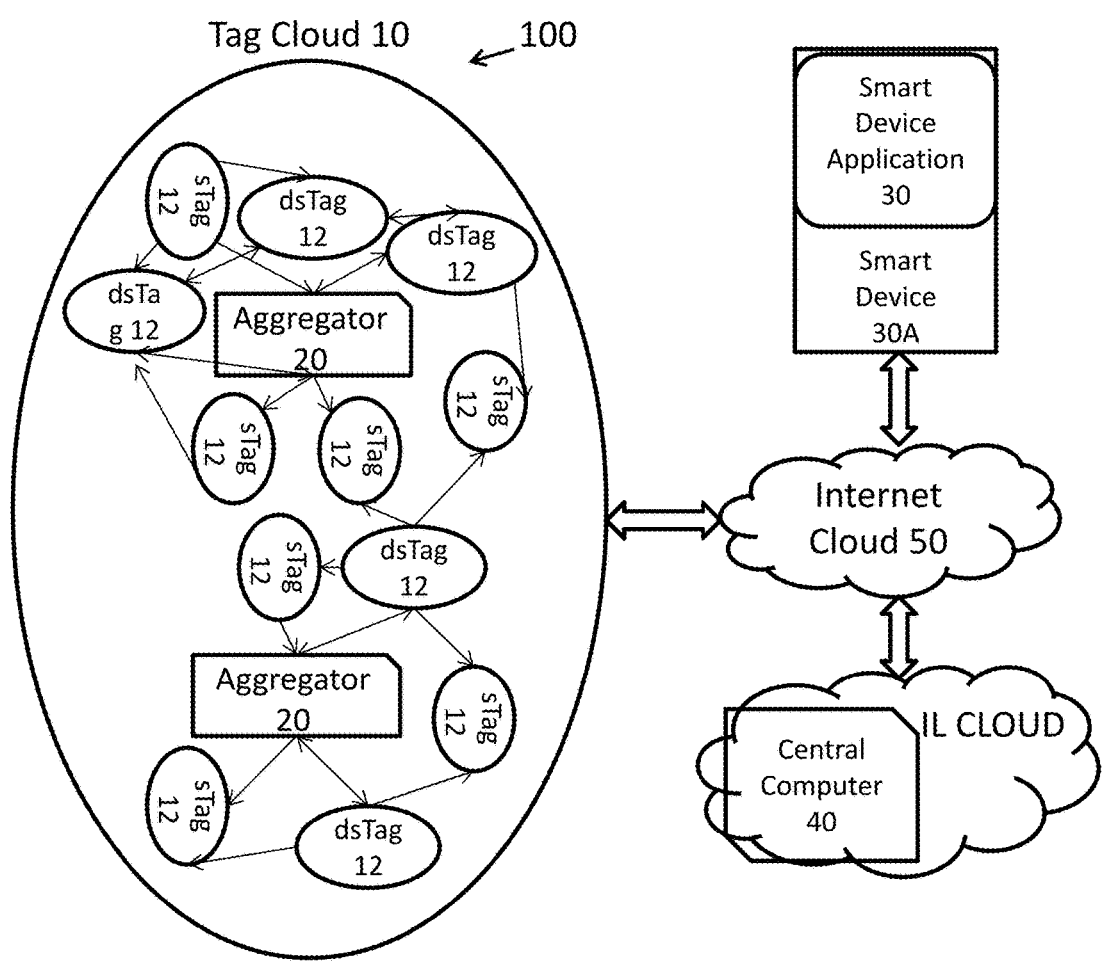
FIG. 1A illustrates a system structure, according to an embodiment of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides methods and systems for a new type of power saving intelligent locating application. The methods and systems of the present disclosure can be produced inexpensively and can have a variety of applications. For example, among other things, applications include tracking consumer traffic within retail environments, helping businesses gather consumer traffic data, gather purchasing data for businesses to better understand their consumers and to assisting consumers locating and buying products within the retail environments. However, it is contemplated the methods and systems of the present disclosure can be used in many different industries and technologies, such as, for example, the consumer goods industry, manufacturing industry, health industry, underwater technologies, robotic system technologies and other similar industries and technologies.

It is contemplated that the methods and systems of the present disclosure can be used in consumer goods and perishables (food industry), where coupled with specific sensors can trigger alarms when certain perishables passed the expiration date. It is possible that the methods and systems of the present disclosure can be used to track patients, assets or even smaller objects such as surgery equipment, drugs, etc. Within the healthcare space, the methods and systems of the present disclosure can monitor and track the usage of a sanitizer pump or detect if there was any activity in a drug container. Another possible aspect the methods and systems of the present disclosure could be used for in the hospitality industry is for a system that can monitor when a customer left a room and provide notice to a cleaning service to be dispatched to make the room ready for the next guest.

In particular, the methods and systems generally relate to tracking a consumer or an object with a smart phone that enters a space, e.g., retail store, hospital, or a space. As the consumer's smart mobile device breaks a geo-fence created by fixed sensors disseminated within the space, an interaction between the fixed sensor and the consumer's smart mobile device triggers a specific application designated for that space. For example, upon the consumer's smart mobile device being triggered, the specific application initiates a signal through the fixed sensor to an aggregator to a central computer and through a cloud-based network via the internet to send a notification to the consumer's smart mobile device to open the specific application for that space. An aggregator, in one embodiment, is a small computer which is powered via an AC adaptor, has on-board memory for off-line storage and RAM. Aggregators, in one embodiment, have a dual radio baseband chipset and antennae able to transmit and receive Wi-Fi and Bluetooth signals simultaneously. Their main function is to receive the Bluetooth signals from the sensors, aggregate them and send them to the Central Computer over a secured Wi-Fi connection. Upon the consumer opening the specific application for that space on the consumer's smart mobile device, the application can provide different types of information to the user, such as product information via a product search engine which can relay a product query to the central computer and then the product search results from the central computer can be sent back to the consumer on the consumer's smart mobile device. The application can provide different types of information to the user including up-to-date product related information, environment information within the space, etc. Other types of information could be coupons for promotional items, in-store location information of a product of interest, indicating to the user how to find the product of interest within the store by using the customer's smart device, and/or price history or price comparisons for the same product in different stores.

According to an embodiment of the present disclosure, the methods and systems provide a radio based system capable of saving battery power for deployed, autonomous radio emitting devices disseminated within a space to form a meshed network. The meshed network of the fixed radio emitting devices create a geo-fence within the space, wherein the fixed radio emitting devices are capable of wirelessly communicating with neighboring fixed radio emitting devices. For example, each fixed radio emitting device or tag is aware of and can be connected to its neighbors and communicate together. The fixed radio emitting devices or tags are connected to aggregators which are in communication with a central computer that is in communication with a cloud-based network via the internet. The radio based system incorporates communication from the fixed radio emitting devices (or tags) (e.g., to aggregators and through the central computer, the cloud-based network) and to smart mobile applications downloaded onto smart devices, e.g., smart phones, tablets, computers, etc.

Overview

Incorporated into embodiments of the present disclosure, the following elements may be included; a tag cloud having tags, aggregators positioned within an approximate the tag cloud, a central computer, a cloud-based network (cloud), a smart device application and a smart device.

For purposes of the present disclosure, a tag can include a wireless transceiver, processor and it can include its own power supply. For example, tags generally can have a Tx/Rx radio front end and the ability to "listen" to its neighbor beacons in order to adjust its power based on surrounding radio activity. A group of tags within a space forming a meshed network may be considered a tag cloud. It is noted that tags can also adjust their Tx power and the transmission interval when instructed through the aggregators by the cloud computer.

By non-limiting example, some types of features of tags may include: (1) Bluetooth tags (sTAG) having HW/SW elements which are fixed or mobile; (2) Duel stack TAG (dsTAG), having a dual BT (Bluetooth) stack able to simultaneously receive on one and transmit on the other; (3) tags communicating with aggregators incorporating multi functions; (4) tags communicating by itself or through other devices with a central computer and (5) tags communicating through other devices (i.e. aggregators, central computer, cloud network) to communicate with an application running on iOS or Andriod or Windows devices. However, other elements are contemplated and may be included which is dependent upon the specific desired configuration.

For purposes of the present disclosure, aggregators can generally communicate with tags, smart device applications, network clouds and provide its own data/information that may be needed for operation via the specific application. Further, the Aggregators 20 can provide information to users and/or get information from users through a graphical user interface or the like. In one embodiment, the aggregators have a graphical user interface.

For purposes of the present disclosure, a smart device application can generally act as a control, location estimation and processing unit for the system. The application may be able to use existing hardware and software of a smart device (such as its screen, input method, communication facility, sensor data etc.).

For purposes of the present disclosure, a smart device may include a Smartphone, a Tablet, a Notebook, a PC, a smart watch (Apple® iWatch®), smart glasses (e.g., Google® Glass®), wearable technology, a cloud based service app, etc.

The central computer may be located anywhere as long as it is connected to the Internet. Further, the central computer can perform functions related to applications which need to be performed and can also be connected with mobile applications distributed on different server devices, e.g., Google®, Apple® and/or Microsoft® servers for the mobile applications distributed on iOS® or Android® or Microsoft® devices. The applications running on iOS® or Android® or Windows® devices can be downloadable and can contain specific applications along with performing specific functions directed by the central computer.

For purposes of the present disclosure, a cloud-based network system or a network cloud can generally be defined as able to provide data storage, processing, and analytics along with other functioning aspects. For example, the system can provide notice alarms, backup data protocols for system data, synchronization and sharing of data between devices and networks, crowd mapping of identified devices and interfacing with the system via cloud based applications.

For purposes of the present disclosure, a meshed network can generally be considered as a type of network topology in which a device, tag or node can transmit its own data as well as serves as a relay for other tags or nodes located near it. The tags or nodes can be wireless using routers to provide for an efficient data transfer path for effective communication. It is noted that the nodes (or aggregators in the meshed network) can also be linked to the internet and the cloud computer via a wireless or Ethernet network.

A power saving intelligent locator system for locating a user within a space, the system comprises providing a tag cloud having multiple tags that communicate tag data with aggregators, wherein the tag cloud and aggregators are located within the space and form a meshed network, the aggregators communicate data to a central computer that is in communication with a cloud-based network. The system provides a user smart device capable of downloading a mobile application wirelessly and wirelessly communicating with an internet system that is in communication with the cloud-based network. The central computer receives information about the user smart device entering the meshed network by wireless tags positioned within the space. The information is obtained by the wireless tags during a recognition process that comprises wirelessly transmitting messages between the wireless tags to aggregators, then wirelessly transmitting the information from the aggregators to the central computer, wherein the central computer communicates with the cloud-based network, wherein the wireless tags transition from a sleep state to an active state. Locations of the user smart device in the space are determined in response to the information, and are used to calibrate information indicative of an actual or estimated location of the user smart device within the space. The cloud-base network receives user smart device information related to a location of the user smart device in relation to wireless tags within the space, for the user to open the mobile application on the user smart device of the user. User smart device information related to a location of the user smart device is received from the user of the user smart device in relation to a subset of the wireless tags. User requested smart device information related to product information, service information, other information or some combination thereof that is requested by user directed to information located within the space is received, from the user of the user smart device. The location of the user smart device within the space is determined in response to the user smart device location information and in response to locations of the wireless tags of the subset of wireless tags in the space, wherein each tag of the tags not within an approximate range of the user smart device within the space receives wireless transmissions from other tags to transition from the active state to the sleep state; and user requested smart device information within the space is determined in response to user requests. Requested smart device information is provided to the smart device of the user, using determined user location information within the space. The requested user information within the space is provided via the wireless tags of the subset of wireless tags in the space and user device mobile application services is provided.

System Structure

FIG. 1A illustrates a system structure 100 including a tag cloud 10, aggregators 20, a smart device application 30, a smart device 30A, a central computer 40 and a cloud-based network (cloud) 50, according to the methods, systems and devices of an embodiment of the present disclosure. For example, the tag cloud 10 can include tags 12 including a group of one or more tags of the same type or multiple tags of different types that can be manipulated by another device. The tag cloud 10 may also include aggregators 20 that can have a function of collecting data from the tags 12; aggregators 20 can send the collected data to a higher level network element, i.e. the central computer 40 and the cloud-based network (cloud) 50, or a separate computer and/or to a separate cloud based computer system.

Aggregators, Tag Cloud and Tags

Figure 1B:
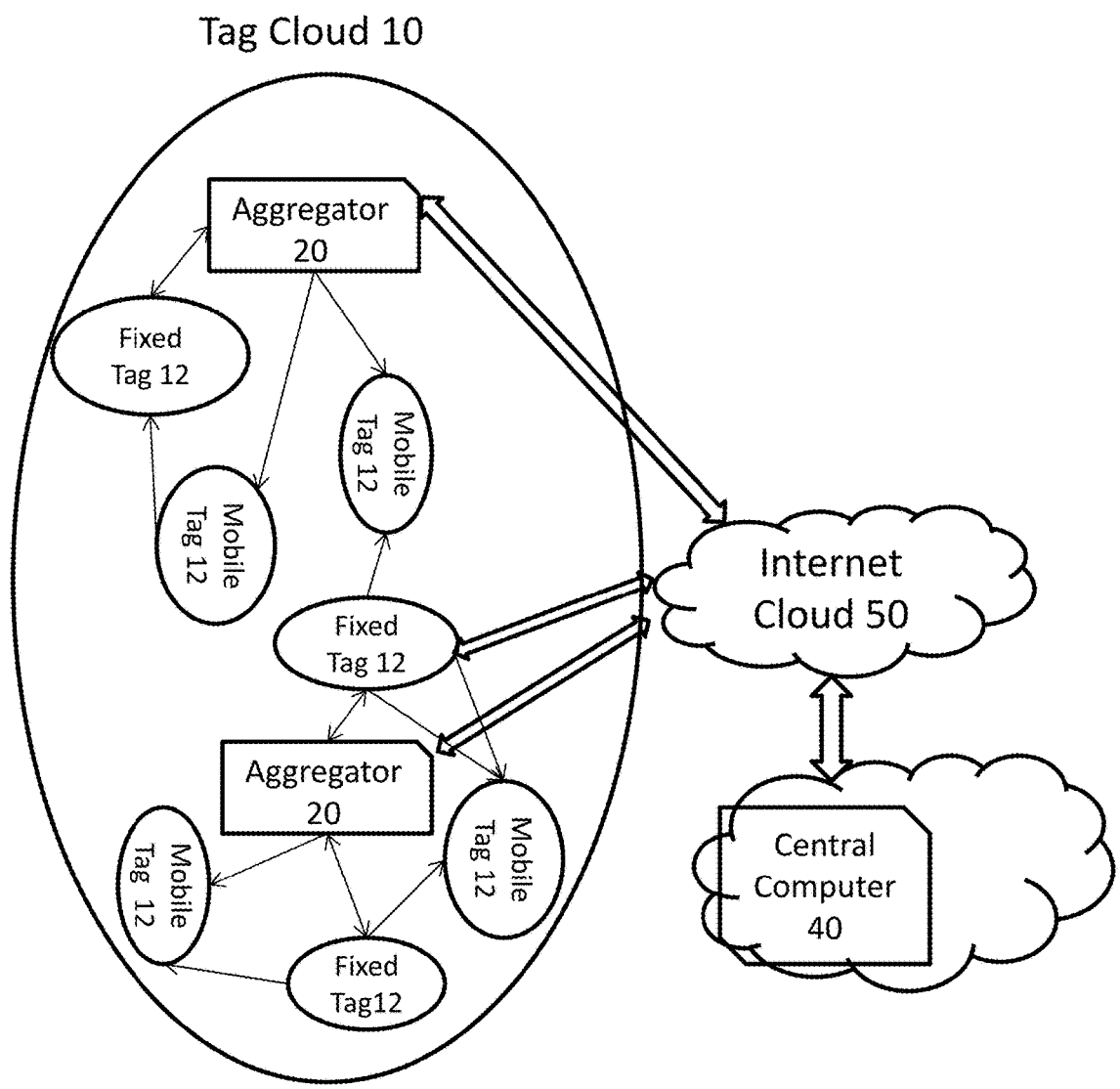
FIG. 1B illustrate tags and aggregators of the system structure that can communicate within the tag cloud and the central computer, according to an embodiment of the present disclosure.

FIG. 1B illustrate tags 12 and aggregators 20 of the system structure 100 that can communicate within the tag cloud 10 and the central computer 40. Some aspects of the tags 12 and aggregators 20 include the ability to "know" when a smart mobile application is active and to "know" the relative location of the interacting device or smart device within the geo-fence in the space.

For example, the tags 12 and aggregators 20 can raise their transmit power and their emitting signal frequency to provide a more accurate function to the intelligent, moving smart device. The tags 12 and aggregators 20 are considered to have two modes of operation, the first mode includes an "active state" when the tags are active having raised transmitting power and transmitting frequency levels, and a second mode or "a sleep state" when the tags 12 and aggregators 20 are not active and do not have raised transmitting power and transmitting frequency levels. For example, as the smart device moves away from a specific location within the geo-fence in the space, the last emitting tag 12 and aggregator 20 (furthest from the smart device) will send a message to the previous tag in the direction of propagation to reduce its transmit power and transmitting frequency levels. In other words, the transmit power and the transmitting frequency levels will transition from an "active state" to a "sleep state" depending upon the proximity of the smart device to each tag with the geo-fence within the space. It is similar to an action of a wave moving through the water, as the back end of the wave becomes calm, the tag 12 and aggregator 20 goes into a "sleep state", as the wave is in an action the tag 12 and aggregator 20 is in an "active state." For example, the tags 12 and aggregators 20 may include a Tx/Rx radio front end and the ability to "listen" to its neighbor tags (sometimes referred to as beacons), in order to adjust its power level based on surrounding radio activity. It is noted that the aggregators could also be battery powered.

There are different types of aggregators 20 that may be incorporated in the methods and systems of the present disclosure. For example, there can be aggregators 20 including stationary aggregators, mobile aggregators or aggregators that can communicate with hardware through software. Aggregators 20 can have one or more of the following functions in communicating with tags 12 within the tag cloud 10 and the central computer 40. For example, aggregators 20 may: (a) read and store the radio power level of each of the tags 12 it connects to; (b) dynamically instruct the tags 12 to Transmit (Tx) power; (c) dynamically instruct the tags 12 of the frequency of their signal; and (d) push new FW (firmware) version(s) to the tags 12. It is noted that there can be at least 2 ways for implementation: (1) first, where the aggregators can be "dumb" and only transmit data and commands back and forth between tags and central computer. Further, this is the centralized architecture which can require more signaling between all entities, so more battery power is used; (2) second, the other way can be push intelligence into the aggregators in order for them to take some decisions locally, without the overhead messaging required with the central computer (this is the distributed architecture).

Still referring to FIG. 1B, tags 12 can be capable of communicating with the aggregator 20 and other tags 12 within the same group (a tag cloud 10) or different groups (e.g., different groups of tag clouds) depending upon the specific configuration. Each tag 12 can provide multiple types of data including: specific identity information, general self-tag information including operation thereof, and communication with, in one embodiment, at least 4 neighboring tags and their information, power level information, operation under different levels of power, e.g., active mode, sleep mode, update mode, etc. Update mode is when a tag is receiving a new firmware update or receives configuration information (e.g. Tx power or transmit frequency). For example, tags 12 incorporated into the embodiments of the present disclosure may include a Tx/Rx radio front end and the ability to "listen" to its neighbor beacons in order to adjust its power based on surrounding radio activity.

For example, a sleep state or sleep mode can be understood for a tag 12 as a non RF power transmitting (TX) state, only the receiver (RX) circuitry is active on a timeslot mode (wakes up at slotted intervals to "listen" for any instructions) or continuously. A wake or active mode may be understood for a tag 12 as a state where the tag 12 transmits information and receives instructions (continuously or in a timeslot mode).

Still referring to FIG. 1B, the types of tags 12 that may be incorporated into the present disclosure include a stationary tag, a smart tag, communication tag, and exterior tag. It is possible a single tag could include one or more types of tag features into a single tag 12. For example, a tag 12 could include the stationary tag feature, a smart tag feature, communication tag feature or some combination thereof. The stationary tag feature pertains to a tag which is fixed in a specific location and only transmits it's identity at a predefined frequency. A smart tag feature is a tag which has the ability to gather information via an interface from an embedded sensor and transmit this information to an aggregator or a communication tag, which is able to connect to an aggregator or another tag to forward information received. As noted above, tags 12 can generally include a wireless transceiver, processor and it can include its own power supply. It is noted that a group of tags can be defined within a space or spaces, and/or having one or more arrangement. It is possible that the stationary tag can be a tag that is fixed to a location within a space that is part of a system to establish its location within the space. The communication tag may be able to communicate with hardware elements via software to interact with the system or systems as in FIG. 1C. An exterior tag can be a tag outside of the system(s) that can be read and provide some other features, aspect or attribute that is not within the system, but can be added via the exterior tag depending on the specific configuration.

It is contemplated the tag(s) 12 and aggregator(s) 20 may have multiple types of features, for example: (1) iBeacon Bluetooth standard Tags (sTAG) that may be a standard type or superior type, including HW/SW elements which are either fixed or mobile (one or more radio transmitters on one or multiple technologies, one or multiple HW interfaces, a processor and power supply circuitry; a SW stack able to receive applications, process and package data for TX or RX over the radio technologies); (2) Dual stack TAG: these have a dual BT stack able to receive on one and transmit on the other on different frequencies; (3) specialized tags able to transmit any kind of information such as temperature, humidity, air quality, Carbone Monoxide level, accelerometer readings (4) fixed aggregators (AGGR), wherein this may include hybrid HW elements such as Bluetooth+Wi-Fi, or Bluetooth+Cellular (GSM, CDMA, HSPA or LTE) or Bluetooth+Cellular+Wi-Fi, or some combination thereof.

Still referring to FIG. 1B, the tags 12 having Bluetooth features, such as a Bluetooth iBeacon 4.0 Low energy (BTLE) can provide many advantages. For example, at least one aspect of having a tag 12 with a Bluetooth feature can be that by forming a meshed network (each tag is aware of and connected to its neighbors, such as, in one embodiment, approximately 4 tag neighbors) and each tag can communicate with each other. Still referring to FIG. 1B, the smart tag can be a stationary tag that can include additional features of functionality to the system including: (a) capable of being able to read other types of sensors such as environmental senses, i.e. temperature, pressure and the like associated with aspects of the space within the tag cloud 10, and (b) capable of being able to receive and send data and upon receiving or sending data commence an action.

Figure 1C:
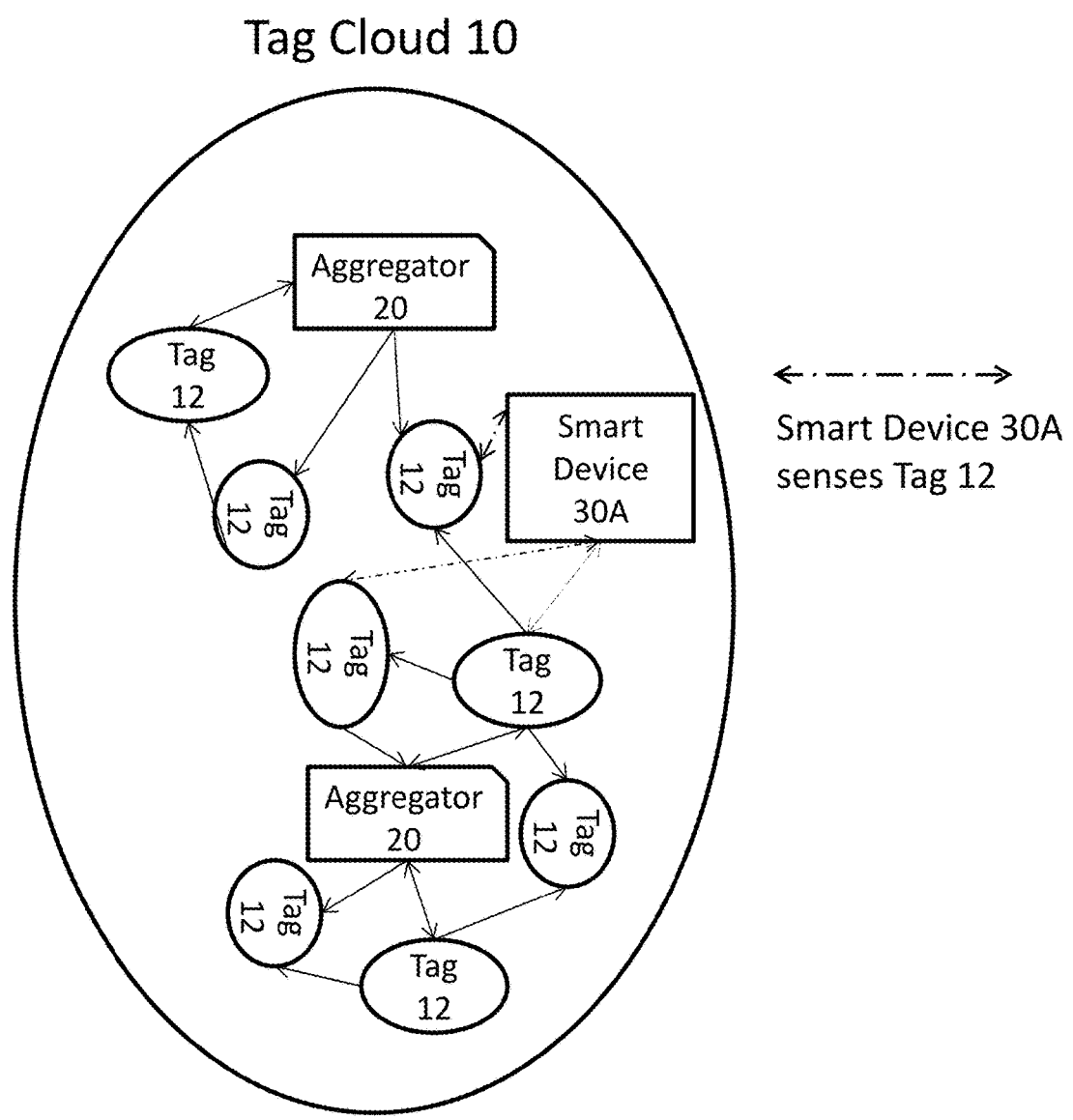
FIG. 1C illustrates a smart device application downloaded on a smart device of the system structure located within a geo-fence within the tag cloud, according to an embodiment of the present disclosure.

FIG. 1C illustrates a smart device application 30 downloaded on the smart device 30A of the system structure 100 located within the geo-fence within the tag cloud 10, wherein the tag(s) 12 and aggregator(s) 20 can communicate with the smart device 30A. For example, the aggregators 20 can provide its own data/information that may be needed for operation via the specific application. Further, the aggregators 20 can provide information to users and/or get information from users through the graphical user interface, such as a smart device 30A including a smart phone, computer, tablet, etc.

Central Computer

Referring to FIG. 1B and FIG. 1C, the central computer 40 according to the present disclosure can perform real time product price comparisons in a specified geographical area and in a product category when prompted by the user. For example, upon a search initiated by a consumer on the consumer's smart mobile device, the central computer 40 can relay the consumer's request to a store where the consumer is currently located. Some features the central computer 40 may be able to perform can include, by non-limiting example:

a) Supplying product information, i.e., price, product specifications, etc.
b) Location of the product nearby being offered for sale near the consumer's location outside of the space.
c) Provide a comparison of the best prices available from the price finder search engine and sends the identified new best price, if necessary, back to the user's smart device's LCD dynamically. The LCD can now display the new best price, the retailer can then advertise to all of its customers that they can provide "The Best Price Guarantee".
d) The central computer 40 will send the consumer smart mobile device the location of the product searched
e) The store application on the consumer's smart mobile device can provide a way to finding products within the space, via an indoor turn by turn navigation-like engine showing the consumer the specific requested area, aisle, shelf where the product is located
f) If the smart mobile device is equipped with a payment method accepted by the store, the consumer may pay directly at their current location within the space, i.e. the shelf where the product is located, so as to save the consumer from wasting additional time at check-out lines.

Other aspects and features of the central computer 40 are contemplated.

Cloud-Based Network (Cloud)

Referring to FIG. 1C, the cloud-based network (cloud) 50 according to the present disclosure can manage secure private networks over the public Internet by utilizing a global cloud computing infrastructure. In cloud-based networking 50, traditional network functions and services including connectivity, security, management and control, are pushed to the cloud and delivered as a service. Cloud-based networks 50 typically require an Internet connection and can work over any physical infrastructure, wired or wireless, public or private. The cloud-based network 50 can provide many aspects, including storage, processing, analytics and other functionality provides value added services. For example, some aspects the cloud-based network 50 can provide include: backup capabilities for system data; synchronization and sharing of information between readers, e.g., smart devices 30A; synchronization between different smart devices applications 30; interfacing the system with cloud based applications; crowd mapping of tagged items; and issuing instructions for unidentified items.

Smart Device Application and Smart Device

The smart device application 30 may act as a control, location estimation and processing unit for the system. The application can use existing hardware and software of the smart device 30A (such as its screen, input method, communication facility, sensor data etc). Examples for a smart device 30A include a Smartphone, a Tablet, a Notebook, a PC, a smart watch, smart glasses, wearable technology, a cloud based service app, etc. The application can perform one or more tasks. For example, (1) configuration and association of tags; (2) Storing historical log of tag position, existence; (3) estimate and display of tags' position, direction; (4) Communication with the network cloud; (5) providing user interface; (6) storing and implementing aspects for tagged items handling; and (7) providing notifications to the user, (8) receive and decode tags and aggregators signals, (9) display location specific information such as building maps, points of interest.

The smart device application 30 network cloud connection can be a wireless connection (e.g. through Bluetooth or WLAN connecting to the internet) or a wired connection (e.g. using a USB cable connecting to a device that is connected to the cloud). This connection can be used to: (1) transfer data from the application to the cloud; (2) transfer data from the cloud to the application (3) synchronize data for different instances of the application through the cloud; (4) control the application from the cloud; (5) Backup and restore the relevant smart phone application data, and the like. FIG. 1 shows that the user can interact, configure and control the system either from the smart device 30A, smart phone application, the tag(s) or from the cloud.

Embodiments of the Present Disclosure

Figure 2A:
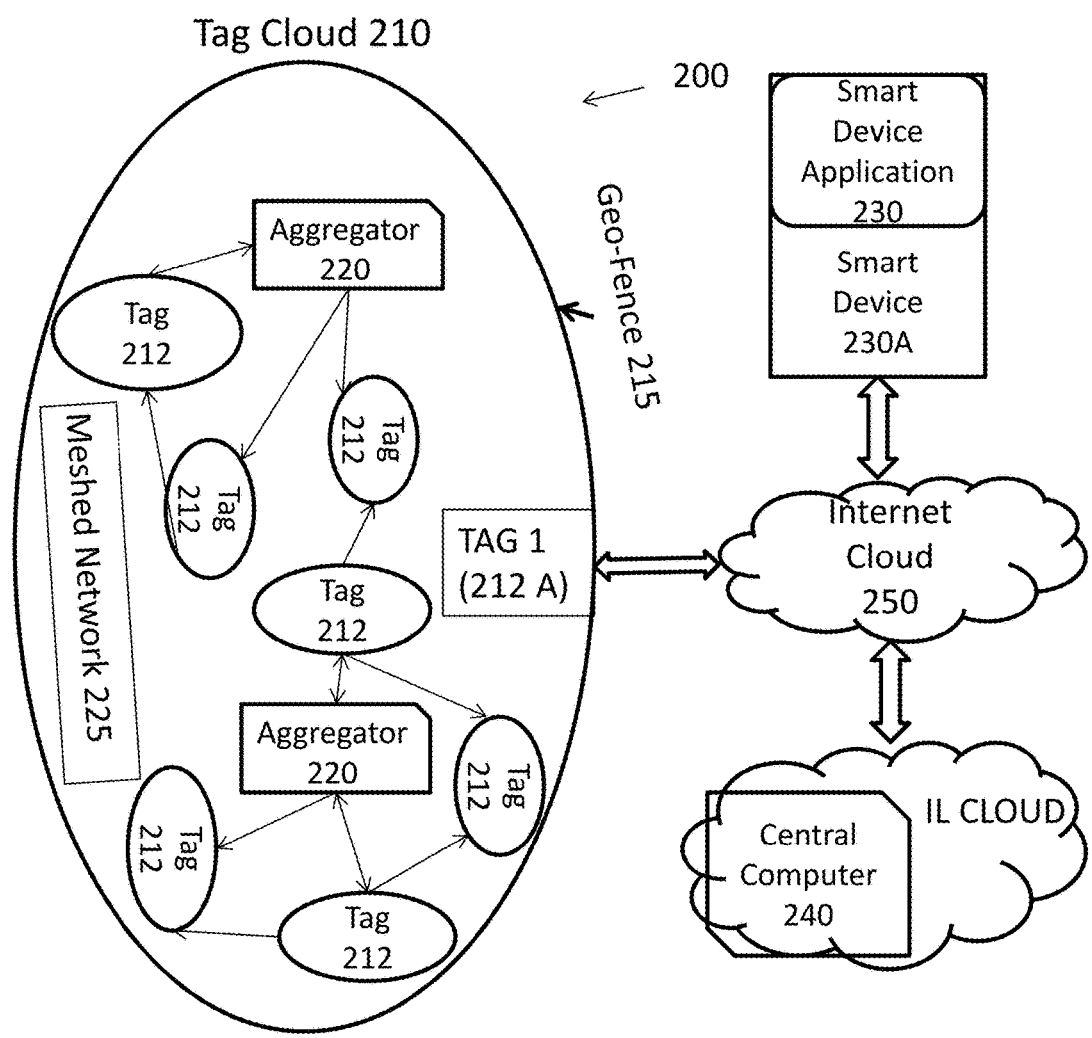
FIG. 2A illustrates an embodiment of a radio based system capable of saving battery power for deployed, autonomous radio emitting devices disseminated within a space to form a geo-fence or meshed network, according to an embodiment of the present disclosure.

FIG. 2A illustrates an embodiment of a radio based system 200 capable of saving battery power for deployed, autonomous radio emitting devices (tag cloud 210 including tags 212, aggregators 220 and at least one TAG1 212A) disseminated within a space 215 to form a geo-fence or meshed network 225. The meshed network includes fixed tags 212 and aggregators 220 positioned strategically in the space 215, wherein the tags 212 and aggregators 220 wirelessly communicate with neighboring fixed tags 212 and aggregators 220 to form a meshed network 225. The fixed tags 212 communicate with aggregators 220 to connect to a central computer 240 that is in communication with a cloud-based network 250 via the internet. The radio based system 200 incorporates communication data gathered from the fixed tags 212 via aggregators 220 through the central computer 240, the cloud-based network 250 to smart mobile applications 230 downloaded onto smart devices 230A.

The fixed tags 212 and aggregators 220 are capable of "knowing" when a smart mobile application 230 is active and by knowing the relative location of the interacting device or smart device 230A within the space 215. For example, the fixed tags 212 and aggregators 220 can raise their transmit power level and their emitting signal frequency levels upon detection of a smart device 230A. For example, as the smart device 230A moves away from a specific location within the geo-fence within the space, the last emitting tag 212 or aggregator 220 (furthest from the smart device 230A) will send a message to the previous tag 212 or aggregator 220 in the direction of propagation to reduce its transmit power and transmitting frequency levels. In other words, the transmit power and the transmitting frequency levels will transition from an "active state" to a "sleep state" depending upon the proximity of the smart device 230A to each tag 212 or aggregator 220 within the geo-fence in the space 215. It is similar to an action of a wave moving thru the water, as the back end of the wave becomes calm, the tag 212 goes into a "sleep state", as the wave is in action the tag 212 is in an "active state." For example, the tags 212 may include a Tx/Rx radio front end and have the ability to "listen" to its neighbor tags (sometimes referred to as beacons), in order to adjust its power level based on surrounding radio activity. In one embodiment, a tag 212 within the space 215 can communicate with at least four of its neighboring tags 212 within the space 215.

Calibrating the Meshed Network

Figure 2B:
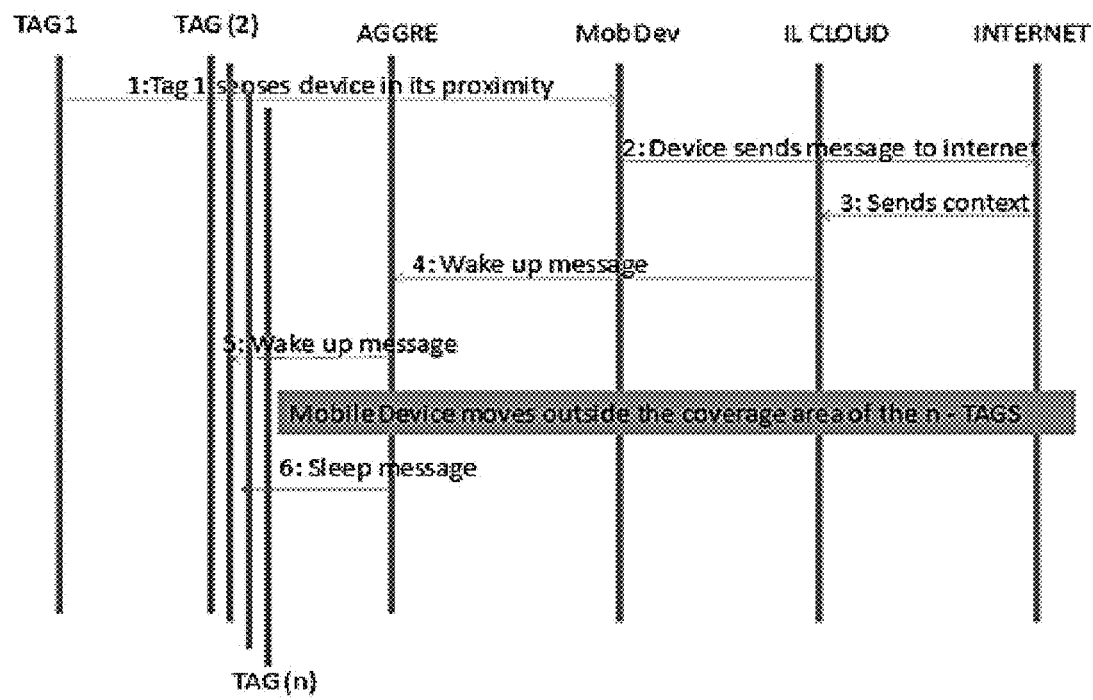
FIG. 2B illustrates an embodiment of the radio based system, after physically placing the tags and aggregators within the space to form the meshed network, where power is later provided to the tags and aggregators so the geo-fence or meshed network can be set up, according to an embodiment of the present disclosure.

Referring to FIG. 2B, after physically placing the tags 212 and aggregators 220 within the space 215 to form the meshed network 225, power can be provided to the tags 212 and aggregators 220 so the geo-fence or meshed network 225 can be set up. For example, after tags 212 and aggregators 220 have been placed in a fixed position and power is applied, each tag 212 and aggregator 220 starts emitting its beacon signal with the maximum transmitting power (i.e. active state). The neighbor beacon listens to all of the beacon signals coming from all of the deployed tags 212 and aggregators 220 and sends the values it recorded to the gateway, i.e. TAG1 212A.

During this initial startup process, the system 200 begins building a map or the geo-fence or meshed network 225. For example, the aggregators 220 "know" the location of each tag 212, i.e. each tag 212 has an ID which it uses in its broadcast. Once the aggregators 220 record the RF powers from each tag 212 regarding the values it recorded from all other tags 212, the Central Computer 240 can begin to: (1) build a map with a neighbor list for each one of the tags 212 and their respective value, for instance, the Central Computer 240 can decide to keep, e.g., four (4) neighbors for each tag 212 with an associated signal strength; (2) the Central Computer 240 can use a learning algorithm to compute the mean and standard deviation for 95% confidence level for each neighbor tag 212 in the list. For example, depending of the mean and standard deviation values, the Central Computer 240 will assign a relative threshold level for, in a one to one relationship, in order to increase maximum likelihood for a location of a tag 212 to be computed with a high degree of certainty.

Figure 2C:
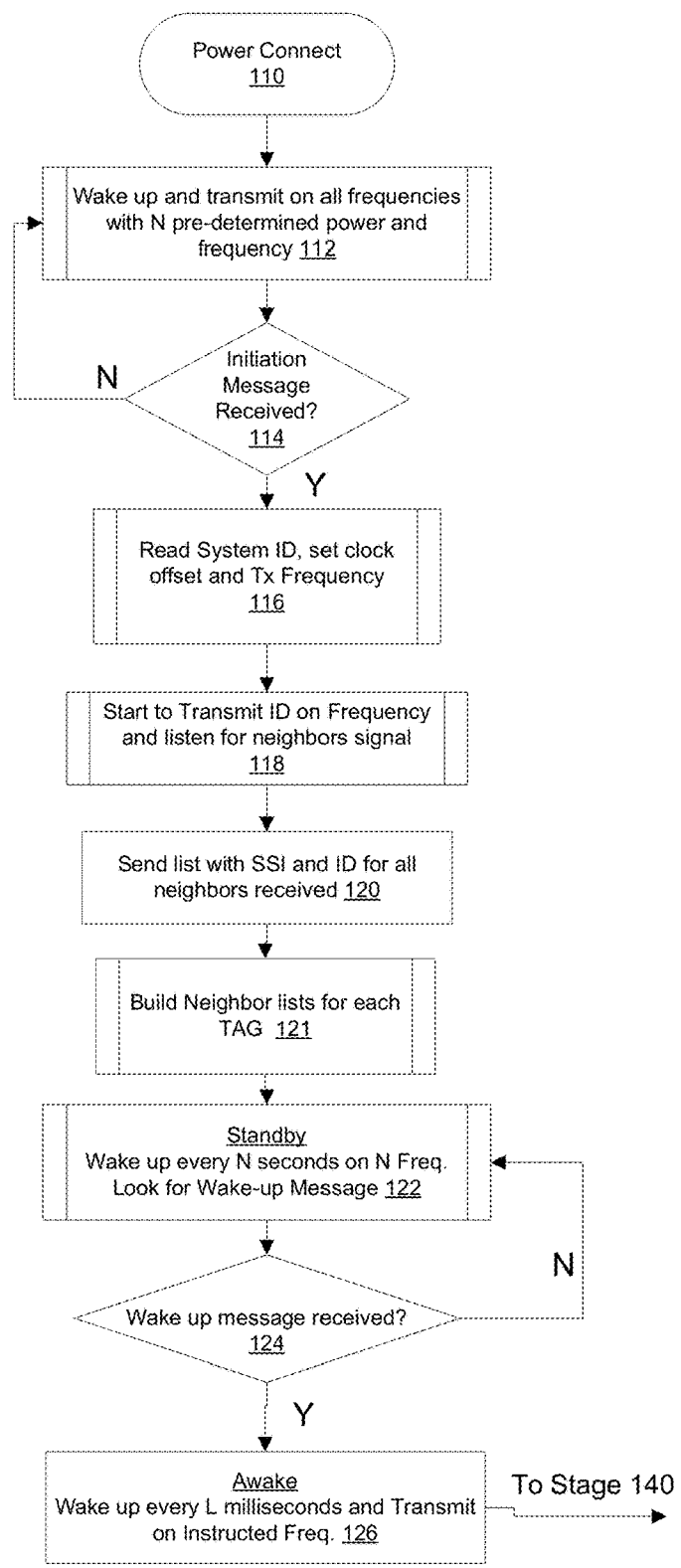
FIG. 2C is a flow diagram illustrating the steps for calibrating the meshed network, according to an embodiment of the present disclosure.

Referring to FIG. 2C, FIG. 2C is a flow diagram illustrating the steps for calibrating the meshed network. Step 110 powers up all components of the meshed network at the specific location. Step 112 illustrates that after the system is powered up, all Tags and Aggregators are transmitting at full power on all pre-programmed frequencies. Step 114 shows that all Tags and Aggregators are listening for configuration (or initiation) message which gives them information about the network. At step 116, the Tags and Aggregators are setting up their clock, transmit frequency for the network. Step 116 shows the Tags and Aggregators will start transmitting and listening to the strongest signals coming from their respective neighbor Tags at step 118. At step 120, all the information about neighbors is relayed to IL CLOUD, At step 121, the IL CLOUD builds a neighbor list for each Tag and Aggregator in the network. At step 122, the system goes into a Standby state, listening and waiting for the Wake up message in order to start normal operation. Step 124 shows that the wake up message arrives at step 124, wherein as the Wake up message arrives for all Tags at step 126, the system is fully awake and operational and starts normal operation based on pre-programmed information relative to power and cycle it needs to transmit.

Radio Based System Initial Operation

Referring to FIG. 2A and FIG. 2B, the radio based system 200 includes at least one TAG1 212A that is located approximately at an entrance of the space 215, for example, at an entrance of a building where the system 200 is deployed. It is contemplated the TAG1 212A could be an aggregator 220 or the like.

In the initial operation of the system 200, the TAG1 212A will sense that a smart device 230A broke the geo-fence it created earlier (i.e. the smart device 230A needs to be approximate the meshed network). The mobile application 230 running on the smart device 230A receives the TAG1 212A signal and sends a message over cellular network to the servers communicating with the Central Computer 240, e.g., IL CLOUD, informing the Central Computer 240 that it is running a certain mobile application. The servers forward the message to the Central Computer 240, e.g., IL CLOUD, with the context received from the application 230 running on the Smart Mobile Device 230A. The Central Computer 240, e.g., IL CLOUD, sends a wake up message to a tag 212 or aggregator 220 where TAG1 212A is registered to belong. The tag 212 or aggregator 220 sends a wake-up message to all neighboring TAGs 212 approximate the TAG1 212A to place them in a wake up state. After the smart mobile device 230A passes the area covered by the n TAGS, the aggregator (AGGR) (or neighbor tags) send a SLEEP message to all n TAGS to resume sleep mode.

Figure 2D:
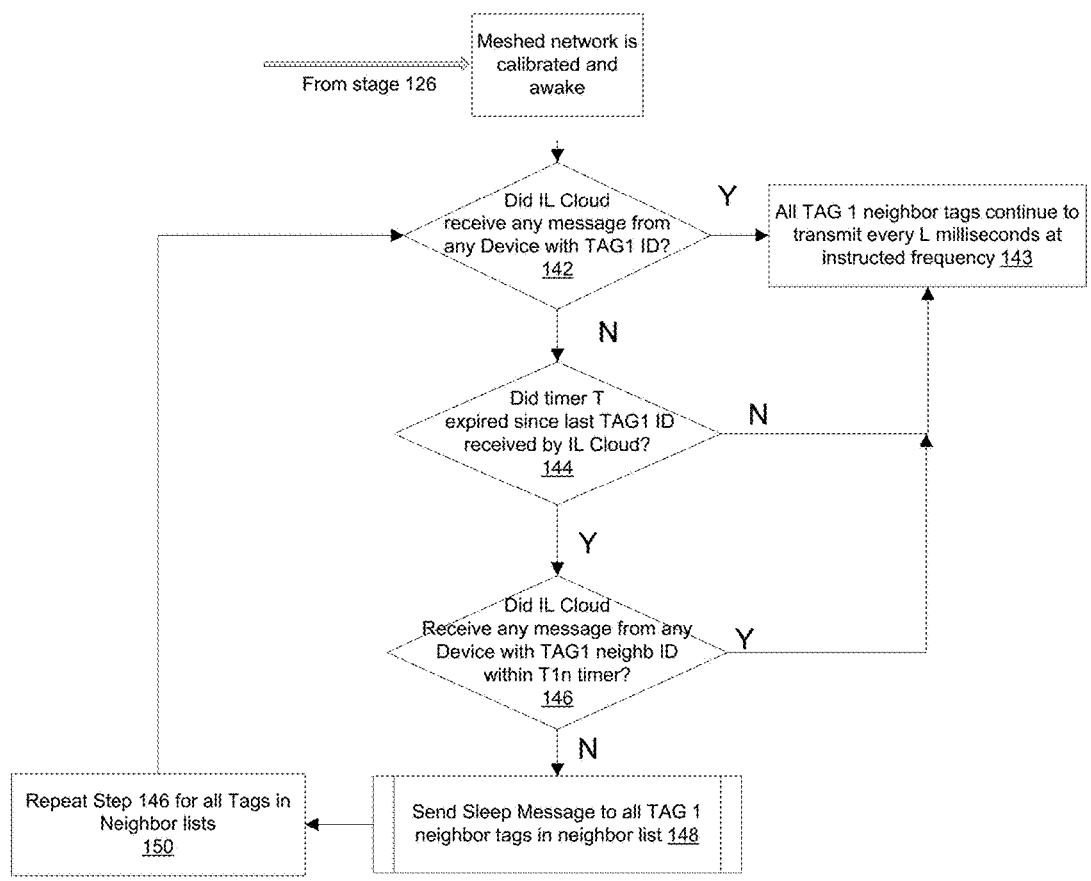
FIG. 2D is a flow diagram illustrating the operation of the meshed network after it was calibrated, according to an embodiment of the present disclosure.

FIG. 2D is a flow diagram illustrating the steps for bringing the radio based system into initial operation. The meshed network is now calibrated and awake. The it CLOUD is looking for messages coming from different smart devices with the correct meshed network identifiers at step 142. At step 143, if any device sends the TAG1 identifier to IL CLOUD, the meshed network will continue its normal (awake) operation. After the last TAG 1 message is received by IL CLOUD from any smart device, a watchdog process running on IL CLOUD starts a timer. The timer is checked by the process at step 144. If the timer did not expire, the process will not take any action and the meshed network will continue its normal (awake) operation. At step 146, if the watchdog process found that the timer expired, that means that there is no activity detected in the meshed network for a T period of time and sleep mode can be activated. At step 148, IL CLOUD sends Sleep Message first to all Tags in the neighbor list of TAG1, then progressively to all Tags in the network at step 150, with the last one being the very last TAG ID received from any smart device.

Figure 3:
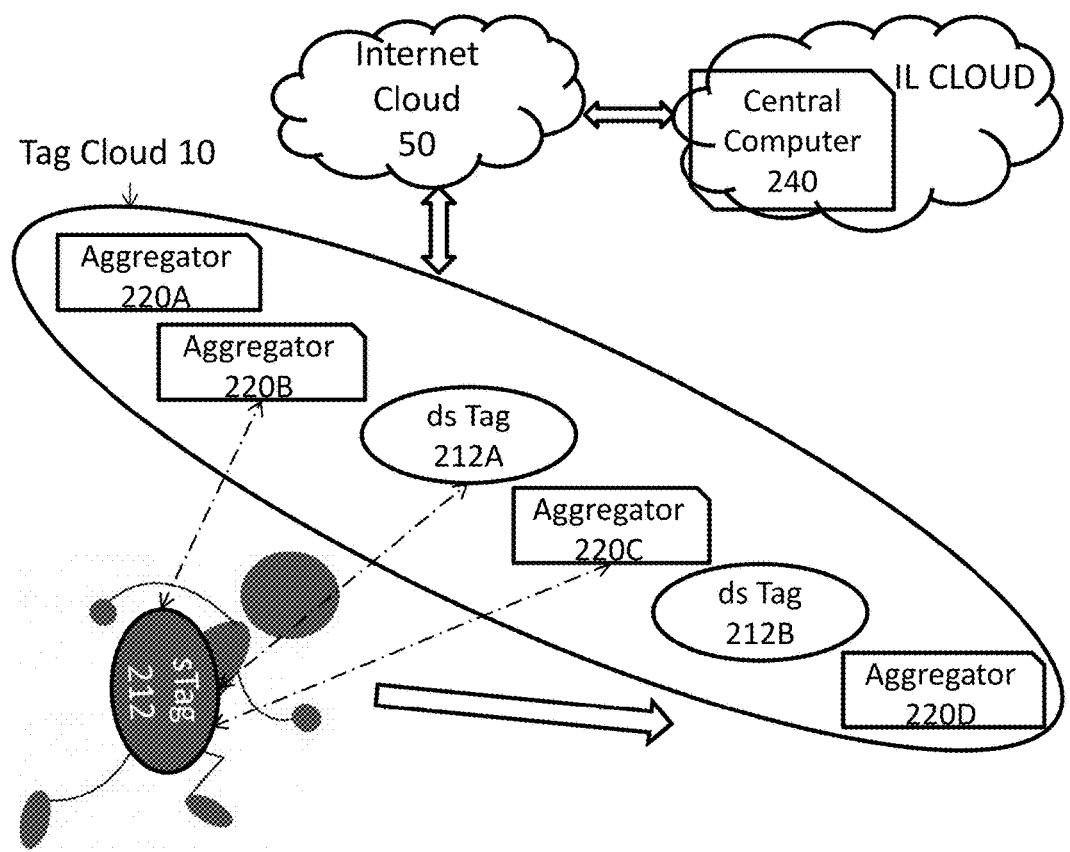
FIG. 3 illustrates a system having fixed tags located within the meshed network that can automatically track people and assets as they move from one position to another within the meshed network or space, according to an embodiment of the present disclosure.

Methods and Systems for Tracking a Person or an Asset Using an IoT Meshed Network Referring to FIG. 3, using the previously described meshed network, these methods and systems can provide a way to automatically track people and assets as they move from one position to another within the meshed network or space.

FIG. 3 shows a system having fixed tags 212 located within the meshed network that can automatically track people and assets as they move from one position to another within the meshed network or space. For example, the fixed tags 212 can be equipped with dual stack and/or be an aggregator 220 that are used to provide the function of automatically tracking people and assets as they move from one position to another within the meshed network or space. It is possible the moving objects can be attached to tags 212 without the dual stack. It is noted that moving objects can be detected by either dual stack tags and/or aggregators. A regular tag can be attached to any moving objects which will be tracked within the area defined by the Tag Cloud. For instance medical devices moving from one OR to another, handicap scooter, computers on rollways, etc.

Every time a standard TAG (sTAG) moves, the AGGR reads its signal strength. To determine whether a sTAG is closer from a specific AGGR (or dual stack TAG), RF signal triangulation is used based on the calibration data provided to the Central Computer. If the RF signal of the sTAG can only be "heard" by two AGGR, then the determination is made based on the relative signal strength heard by the two aggregators (using a hysteresis).

Every time a sTAG was determined to have a new location, a time stamp is recorded at the time the event occurred and stored in the central computer for further processing. The Central computer (or IL CLOUD) can also send event push notifications to smart mobile devices registered to receive events for specific sTAG IDs.

Methods and Systems Providing Automatic Check-in Using a Meshed IoT Network.

Figure 4A:
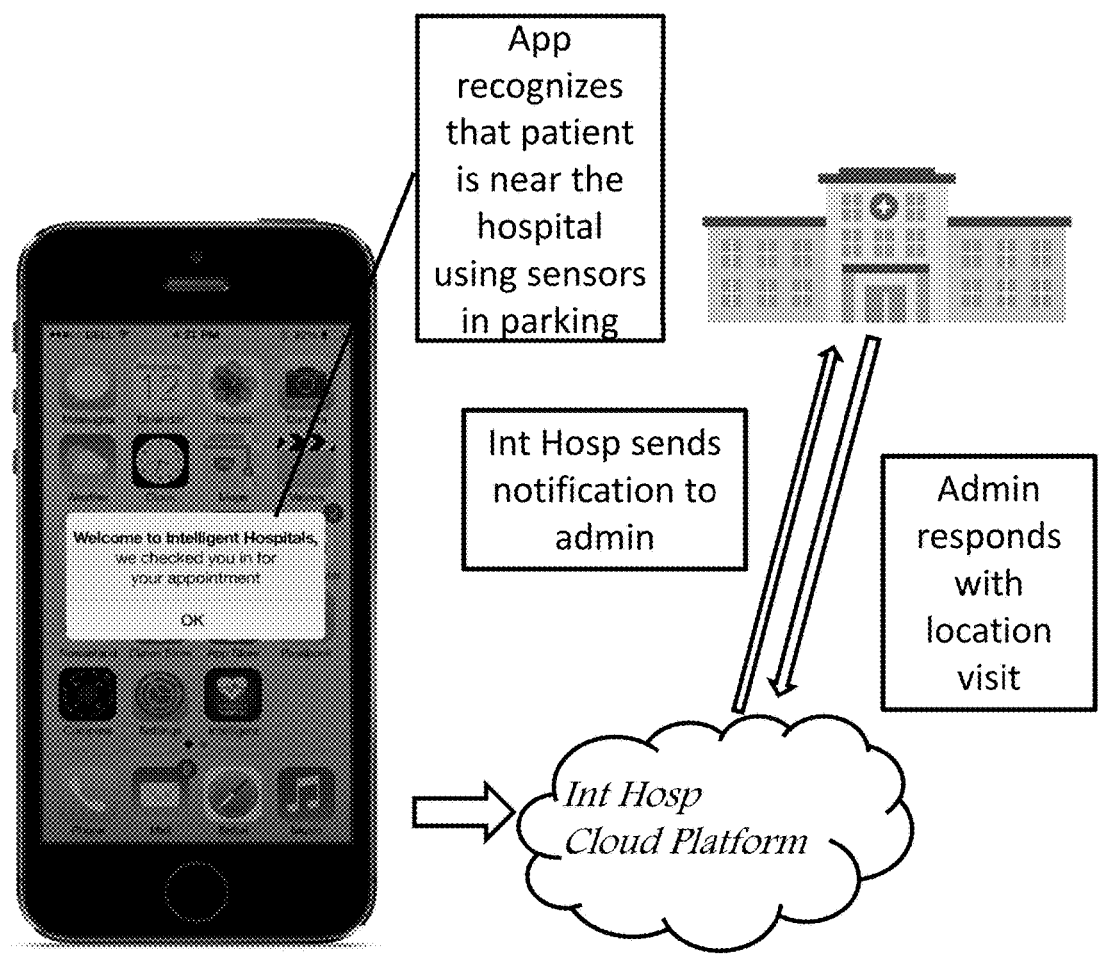
FIG. 4A illustrates a system that can be connected to a healthcare Administrator system in charge of appointment scheduling for patients within the healthcare industry, according to an embodiment of the present disclosure.
Figure 4B:
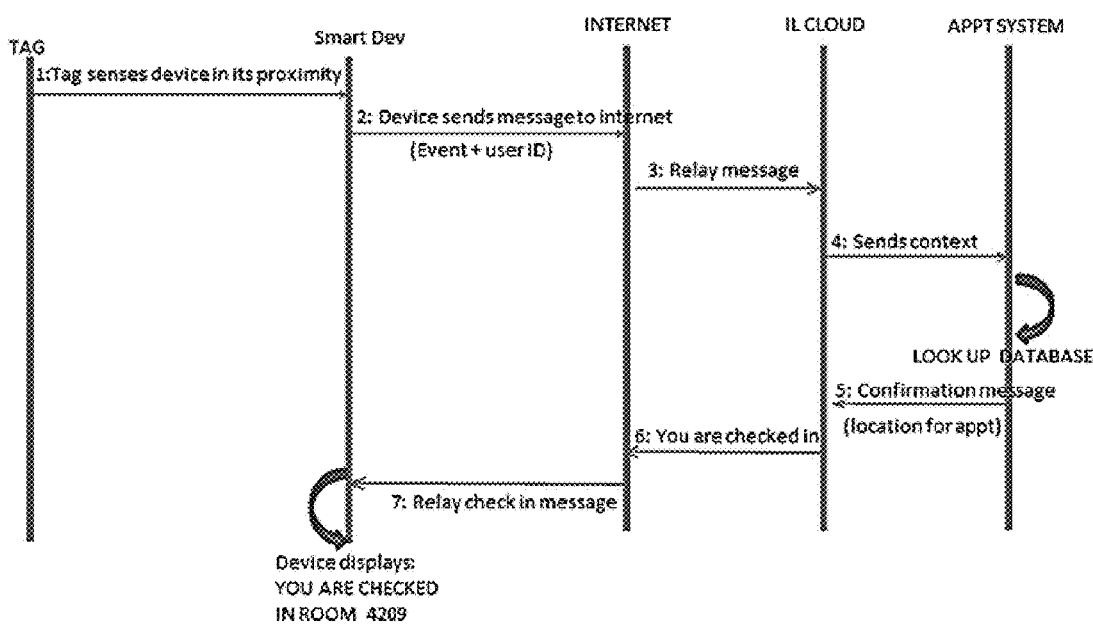
FIG. 4B is a flow diagram illustrating the steps for connecting the system to a healthcare Administrator system in charge of appointment scheduling for patients within the healthcare industry, according to an embodiment of the present disclosure.

Referring to FIG. 4A and FIG. 4B, in a previously described meshed network, a user using a mobile device can be running a specific mobile application. This specific mobile application can have the ability to interface with the meshed network which automatically senses when the device breaks the geo-fence it created in a particular location (indoor or outdoor) or space.

FIG. 4A illustrates a system connected to a healthcare scheduling system in charge of appointment scheduling for patients within the healthcare industry. For example, a hospital (or any office space, doctor's practices, etc.) often can use independent scheduling systems or integrated scheduling systems into their overall IT infrastructure. The meshed network needs to communicate with this scheduling system in order to provide the service. The scheduling system allows the personnel to make appointments for patients. In the meshed network of the present disclosure, a patient using a dedicated application (or a feature of the application) is able to be "checked" in automatically without human intervention. The patient/user must be signed into the application with a unique ID/password combination. The identity of the user is locally encrypted by the application and also stored (encrypted) on the IL CLOUD. Upon entering the area defined by the Tag Cloud, the user breaks the geo-fence established by the Tag Cloud. TAG1 (212A) is sensed by the user's smart device and a message is generated, via servers to the IL CLOUD with the contextual information (user ID, TAG1(212A) identifier & time stamp). The IL CLOUD ID matches the user profile it stores in its database and sends event based contextual information to the Scheduling system, which can inform the personnel of the location of the patient/customer. This process can be repeated multiple times, every time an aggregator/Dual Stack Tag detects the patient/customer on his way to the final destination. Upon reaching the final destination defined in the application running on the smart device by the location of the last aggregator reached (e.g Urology, X-Ray, etc), the meshed network sends the Scheduling system a new message indicating that the patient/customer reached the destination. At that point, the Scheduling system can set the status of the patient/customer as "checked in". If the Scheduling system is integrated with the hospital's/doctor's office EMR (Electronic Medical Records), then the Scheduling system can send the patient's EMR information for verification on the patient's smart device. If the records are unchanged, the patient simply "confirms" that the information is correct using the application. If the information is obsolete, the patient can modify and input updates (such as new address, new insurance information, etc) using the application on its smart device and "commit" changes which will be saved in the EMR.

The user can have already downloaded a correct healthcare application on their smart device that uniquely identifies each patient, for example by a user ID & Password.

As soon as the geo-fence is broken by the smart device, the IL system sends a notification message to the healthcare Administrator system informing it that User X arrived on the premises or within the space. The healthcare Administrator system can check the identity of User X and match the records stored in its own database. If the records match, healthcare Administrator system checks in User X for his/her appointment.

If Administrator system contains the EMR records of User X and if User X is allowed to preview its personal information via the application running on the mobile device, than User X can check that all personal information is correct and commit any changes made via the application running on the mobile device.

FIG. 4B is a flow diagram illustrating the steps for connecting the system to a healthcare Administrator system in charge of appointment scheduling for patients within the healthcare industry.

Figure 5A:
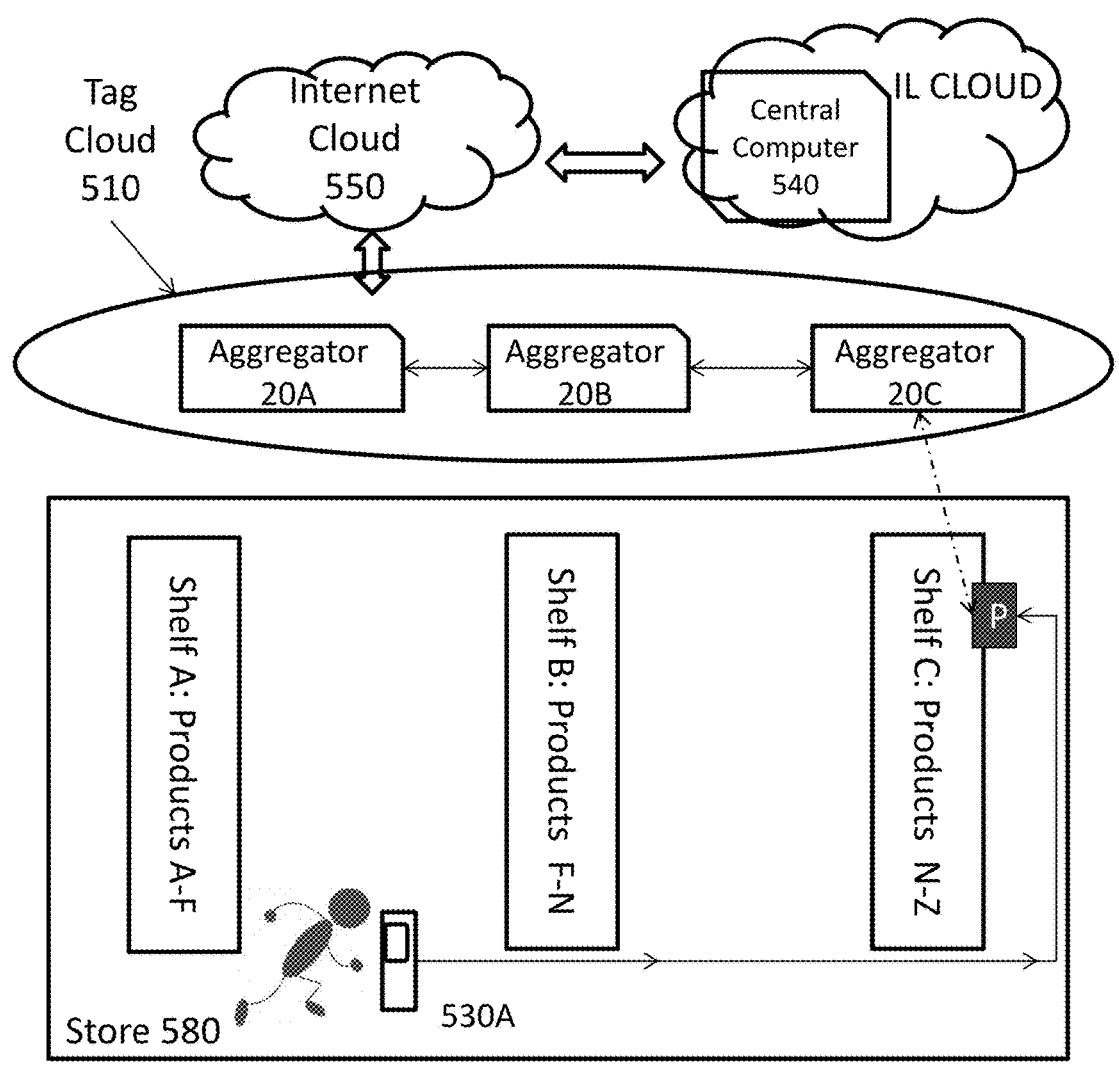
FIG. 5A illustrates a system that connects to a consumer related system that can direct consumers to consumer objects of interests, provide the consumer with real-time pricing information specific to the consumer objects of interests as well as initialize payment methods for the consumer to purchase the consumer objects of interests at the location of the objects of interests in the space, according to an embodiment of the present disclosure.
Figure 5B:
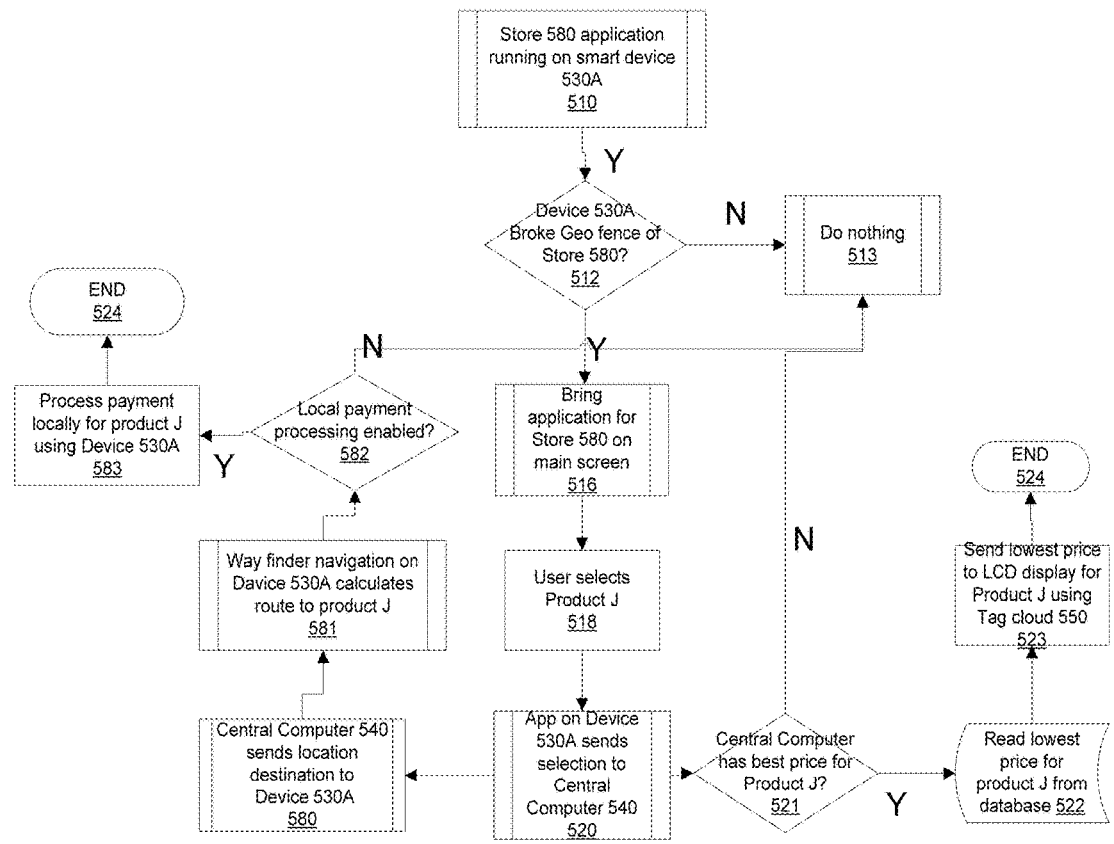
FIG. 5B is a flow diagram illustrating the steps of FIG. 5A, FIG. 5B describes that steps of directing consumers to consumer objects of interests, providing consumers with real-time pricing information specific to the consumer objects of interests as well as the steps of providing initialized payment methods for the consumer to purchase the consumer objects of interests at the location of the objects of interests in the space, according to an embodiment of the present disclosure.

Method and System for Finding an Object in a Store, Providing Object Pricing Information and Payment Methods Thereof Referring to FIG. 5A and FIG. 5B, in a previously described meshed network, a user using a mobile smart device is running a specific mobile application. This specific mobile application has the ability to interface with the meshed network which automatically senses when the mobile smart device breaks the geo-fence it created in a particular location (indoor or outdoor).

FIG. 5A illustrates a system that can be connected to a consumer related system and can direct consumers to consumer objects of interests, provide the consumer with real-time pricing information specific to the consumer objects of interests as well as initialize payment methods for the consumer to purchase the consumer objects of interests at the location of the objects of interests in the space. For example, the consumer store (or warehouse) can be equipped with sensors allowing geo-fencing sensing and triggering for a smart mobile device entering the consumer store. It is possible the store can be equipped with sensors allowing a smart device to be provided with an indoor directional finding, i.e. navigation method. Further, the store may be equipped with LCD pricing displays, e.g., for each individual product, which can communicate via a bi-directional wireless radio interface with a centralized computer system. The smart mobile device can be running the store specific application in the background, while the store centralized computer is connected with a web based price finder engine which finds all competitor's prices for specific products in real time within the consumer's approximate location. It is also possible that the LCD pricing display can have the ability to receive payment information from smart devices and process payments directly via the bi-directional wireless interface while the consumer is located at the product location within the consumer store.

FIG. 5B is a flow diagram illustrating the steps for directing consumers to consumer objects of interests (e.g., products, etc.), provide the consumer with pricing information specific to the consumer objects of interests as well as initial payment methods for the consumer to purchase the consumer objects of interests within a consumer space, e.g., consumer store or warehouse.

A. Directing Consumers to Objects of Interest within the Consumer Space

Step 510 is a pre-requisite where the consumer's smart mobile device has the store specific application installed and running in the background. Step 512 begins when a consumer enters the store; its smart mobile device breaks the geo-fence created by the fixed sensors disseminated around the store facility. At step 516, the interaction between the sensor and the smart mobile device can trigger the store specific application to come up or to send a notification to the user to open the store specific application. At step 518, the application contains (either locally on the smart device or remotely on the central computer) the product categories and individual products for each category. The user, via a drop down menu or via a voice recognition engine specific to the application, selects the product category and then the exact product it intends to purchase (or review).

At step 520, once the product was selected, the smart device sends the product ID to the IL CLOUD which then relays it to the store. At step 580, since each one of the products has a unique TAG ID connected to the LCD display, the meshed network "knows" which TAG ID corresponds to the sought product (destination). At step 581, the application on consumer's smart mobile device calculates the in-store route (area, aisle, shelf where the product is located) and initiates an indoor navigation application on consumer's smart device from the current position (departure point computed by aggregators/dual stack tags). The application will constantly update the consumer on its location in real time relative to the destination.

B. Providing Consumers with Pricing Information Specific to the Consumer Objects of Interests Regarding Step 520, the application provides a product search engine which relays the product query to the central computer and the results from the central computer back to the user on its smart mobile device. Step 521 checks that the central computer can perform real time product price comparisons in a specified geographical area and in a product category. Upon a search initiated by the consumer on its smart mobile device, the central computer relays the request to the store where the consumer is located, and: at Step 522, checks the best price available from the price finder engine; at Step 523, sends the new price—if necessary—to the LCD dynamically. The LCD will now display the new price—the retailer can then advertise to all of its customers that they can provide "The Best Price Guarantee".

C. Payment Methods for Consumer to Purchase Consumer Objects of Interests within the Consumer Space Step 582, if the smart mobile device is equipped with a payment method accepted by the store, the consumer can pay directly at the shelf, avoiding wasting additional time at the cash register. The store specific application can inform the consumer if the store is equipped with such a localized payment system. Each LCD display can be equipped with either NFC technology used today in Google® Wallet and Apple® Pay. The transaction between the device and the NCF chip located in the display is securely relayed by the sTag to the aggregator or dual stack tags to the central computer for processing. Once the transaction is successful, the smart device will show the receipt for the purchase product. The consumer can then show this receipt (on the smart device) to the store clerk upon exiting the store. Any other methods of payment (outside NFC technology) are also possible pending that the store supports it (2D bar code systems, etc).

Figure 6A:
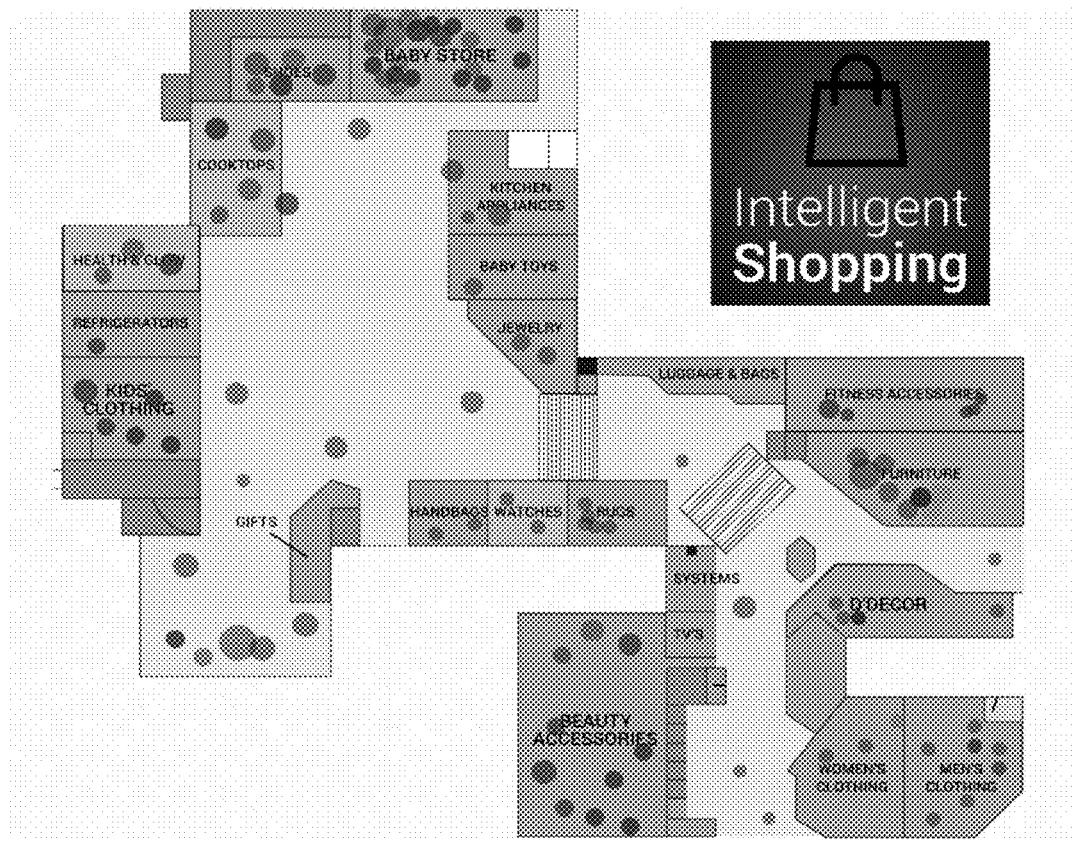
FIG. 6A illustrates the density and spread of consumer movement within the store or warehouse, according to an embodiment of the present disclosure.
Figure 6B:
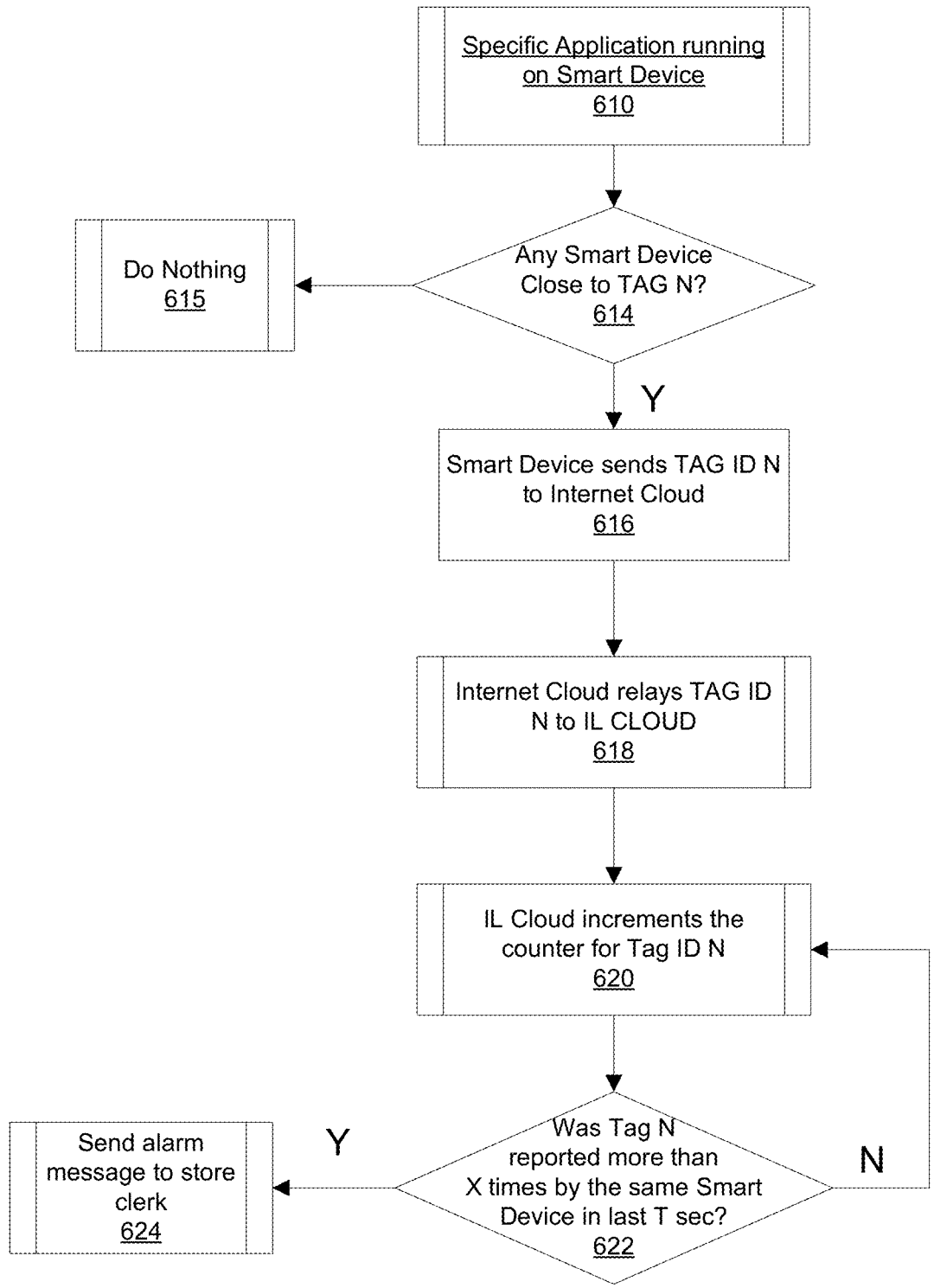
FIG. 6B is a flow diagram illustrating the steps of FIG. 6A.

Method and System for Building a Heat Map, Real Time Learning Based Adjustable Threshold Settings and Alarm Generation Referring to FIG. 6A and FIG. 6B, in a previously described meshed network, a user using a mobile device can run a specific mobile application. This specific mobile application has the ability to interface with the meshed network which automatically senses when the device breaks the geo-fence it created in a particular location (indoor or outdoor).

FIG. 6A illustrates a system and method for the store managers to gather data specific to the consumer's movement within a consumer store or warehouse. Specifically, the data provided can include "knowing" where the customers move inside the stores. For example, the data could include where the consumers spend the most time within a certain location within the store. The data may be able to provide actionable measures for the store manager to better understand and direct or enable consumer spending.

Still referring to FIG. 6A, the user must have the store application running on it's mobile device in the background for the system and method to operate. For example, every time the user's device comes within an X dB signal from a tag, the application on the mobile device can record and store the TAG ID and send it to the system, which can later be accessed by the store manager. It is possible that every 30 seconds, the mobile app can send all the information collected to the Central Computer, e.g., IL CLOUD (via Internet), which computes a "heat map" from all devices sending similar information.

If the application on mobile device receives a preset (Phi) threshold (absolute number) of the same TAG(s) ID (meaning that the user is stationary in a specific location of the store), the application will send a contextual message to the Store system. The context is translated by the IL CLOUD to be the exact place where the information was recorded (e.g., woman's shoes—running shoes). Upon reception of the contextual information by the Store system, if a promotion is ongoing for that particular item type, the store will send the promotion information to IL CLOUD which in return will send a "push notification" to the user's mobile device with the details of the promotion. If a promotion is not available, the IL CLOUD can send a push notification to a store clerk—either on his/her mobile device if clerk is registered to the store Customer Relationship Management system) or to an internal central monitor system, informing them that the person needs assistance—actionable intelligence.

FIG. 6B is a flow diagram illustrating the steps for a store manager to gather data specific to the consumer's movement within the consumer store or warehouse. The previously defined meshed network is implemented in a department store or warehouse. Tags are placed all around the floors and their TAG ID's are input into a database stored in the IL CLOUD and identifying specific areas such as "Men's shoes", "Kids apparel", etc. It can be completely independent of the store IT systems or able to communicate with it via a jointly defined interface or an API. Consumers have previously downloaded a store specific mobile application running on their smart device. The consumer can decide to identify itself by providing a log in information via the application or decide to be anonymous. If the log in is provided, the store can push personalized, location based messages to the consumer. If the consumer did not provide log in information, personalized messaging is not possible—only generic communication can be done.

Further referring to FIG. 6B, the pre-requisite in step 610 requires the user to have installed the store specific application on its smart mobile device. Step 614 checks if any smart mobile device is in close proximity of a Tag. If that is the case, the smart mobile device will send the TAG ID to IL CLOUD in steps 616 and 618, relayed by the Internet cloud. Step 620 refers to a process running on the IL CLOUD which takes into account each message, from any smart mobile devices where for each TAG ID, it keeps a counter and increments the counter each time the TAG ID is reported.

Step 622 refers to another process where each time a specific TAG ID is reported, a timer is started for each Tag. At step 624, if the process at 622 finds that the same smart mobile device reported the same TAG ID a configurable number of times within a configurable amount of time, it will generate an alarm routed from IL CLOUD to the store internal system to inform the clerk that a user may be needing help.

The smart device is able to send information to IL CLOUD either via the store's Wi-Fi system or via the carrier cellular networks (Verizon, AT&T, etc). Each time the user's smart device senses one or multiple tags, it sends the Tags ID to the IL CLOUD which increments a counter for each TAG ID received and assigns a time information for each Tag ID and each event. The information is then computed in real time and a "heat map" is generated, where the hottest area has the larger number of counts for a defined period of time. The IL CLOUD counts the TAG IDs it receives, even if received from the same device. The algorithm implemented in the IL CLOUD will generate an alarm if the same X number of TAG ID's are reported by the same or multiple devices within a pre-defined Y seconds. The values of X and Y are variable and defined based on the store configuration, customer profile (if customer provided log in information, the system will know if it is a repeat user or only someone who likes to browse but not buy) and time of day.

The heat map data can be used by the store manager to correlate the traffic in the store with the cash register sales value either by minute, hour, day, week or month. The real time nature of the information received can generate real time actions—such as sending a clerk to "hot" area or to open another cash register—or longer time actions such as expanding a "hot" area, removing a "cold" one, changing the product mix and product volume, products displayed, etc.

Method and System for Detecting the Sanitizing Pump Usage by a Person Wearing a Tag in a Meshed Network In hospitals or any other industries where the usage of sanitizing equipment is mandatory, the algorithm described in FIG. 7 will provide a method to track the personnel who is using the sanitizer pumps placed at fixed locations within the facility. Each pump has a fixed location and is equipped with an accelerometer sensor connected to a sTag. The accelerometer is attached to the dispenser mechanism and detects movement over 3 axes in space: x, y and z. The hospital personnel wears a sTag attached to their identity badge or any other way. The correlation between the sTag identifier and the personnel identity is stored securely in the IL CLOUD central computer database. Each time the accelerometer detects an event, this event is relayed to the central computer and the algorithm is used to detect the identity of the personnel who used the sanitizer pump. The central computer will keep track of all events and can compute statistics as to who, when, where, frequency of usage, etc. We can also envisage additional intelligence built into the central computer where the meshed network sends reminders to the personnel's smart mobile device to remind them to use the sanitizer dispenser based on specific locations such as Operating Rooms.

FIG. 7 describes the algorithm to detect the usage of the sanitizer dispenser located in an area covered by a meshed network. For the algorithm to work, each sanitizer pump needs to have a pre-calibrated value of its own Signal Strength Indicator (SSI) value which is seen by the closest Aggregators which are N (Closest), N−1 (next closest in one direction) and N+1 (next closest in the opposite direction).

At Step 710, the meshed network is looking to see if any Tags are detected near the location of the sanitizer pump. At step 712, if any are detected, the meshed network will instruct the detected Tags to increase their rate of transmission and keep the transmission power constant. Step 714 gathers as many SSI samples from any detected Tags and computes a mean value for each one of them against the SSI value of the sanitizer pump within the standard deviation range.

Step 716 records the event of the accelerometer changing the Z value, meaning that the pump was auctioned. Step 718 compares the signal of a particular Tag Alpha (nominated tag, meaning that the tag belongs to a person) detected in step 714 to the SSI of the pump and the calibrated standard deviation of that signal after step 716 was recorded. Step 720 compares the signal of a particular Tag Alpha detected in step 714 received by one of the neighbors to determine if the person wearing the Tag Alpha is getting further away from the sanitizer pump. Step 722 makes the determination that person wearing Tag Alpha used the sanitizer pump. Step 724 instructs the Tag Alpha to resume normal frequency of transmission. Step 726 records the event of the usage of the pump by the person wearing Tag Alpha and stores it in IL CLOUD.

The present disclosure is described with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

For the purposes of this disclosure a computer readable medium (or computer-readable storage medium/media) stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure the term "server" or central computer should be understood to refer to a service point which provides processing, database, and communication facilities. By way of example, and not limitation, the term "server" or central computer can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure, a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a wired or wireless line or link, for example.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly.

A wireless network may further employ a plurality of network access technologies, including Wi-Fi, Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For purposes of this disclosure, a client device, such as, for example, a smart device, a tag, or an aggregator, may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device, a Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

A client device may vary in terms of capabilities or features. Claimed subject matter is intended to cover a wide range of potential variations. For example, a simple smart phone, phablet or tablet may include a numeric keypad or a display of limited functionality, such as a monochrome liquid crystal display (LCD) for displaying text. In contrast, however, as another example, a web-enabled client device may include a high-resolution screen, one or more physical or virtual keyboards, mass storage, one or more accelerometers, one or more gyroscopes, global positioning system (GPS) or other location-identifying type capability, or a display with a high degree of functionality, such as a touch-sensitive color 2D or 3D display, for example.

A client device may include or may execute a variety of operating systems, including a personal computer operating system, such as a Windows, iOS or Linux, or a mobile operating system, such as iOS, Android, or Windows Mobile, or the like.

A client device may include or may execute a variety of possible applications, such as a client software application enabling communication with other devices, such as communicating one or more messages, such as via email, for example Yahoo!® Mail, short message service (SMS), or multimedia message service (MMS), for example Yahoo! Messenger®, including via a network, such as a social network, including, for example, Tumblr®, Facebook®, LinkedIn®, Twitter®, Flickr®, or Google+®, Instagram™, to provide only a few possible examples. A client device may also include or execute an application to communicate content, such as, for example, textual content, multimedia content, or the like. A client device may also include or execute an application to perform a variety of possible tasks, such as browsing, searching, playing or displaying various forms of content, including locally stored or streamed video, or games. The foregoing is provided to illustrate that claimed subject matter is intended to include a wide range of possible features or capabilities.

Figure 8:
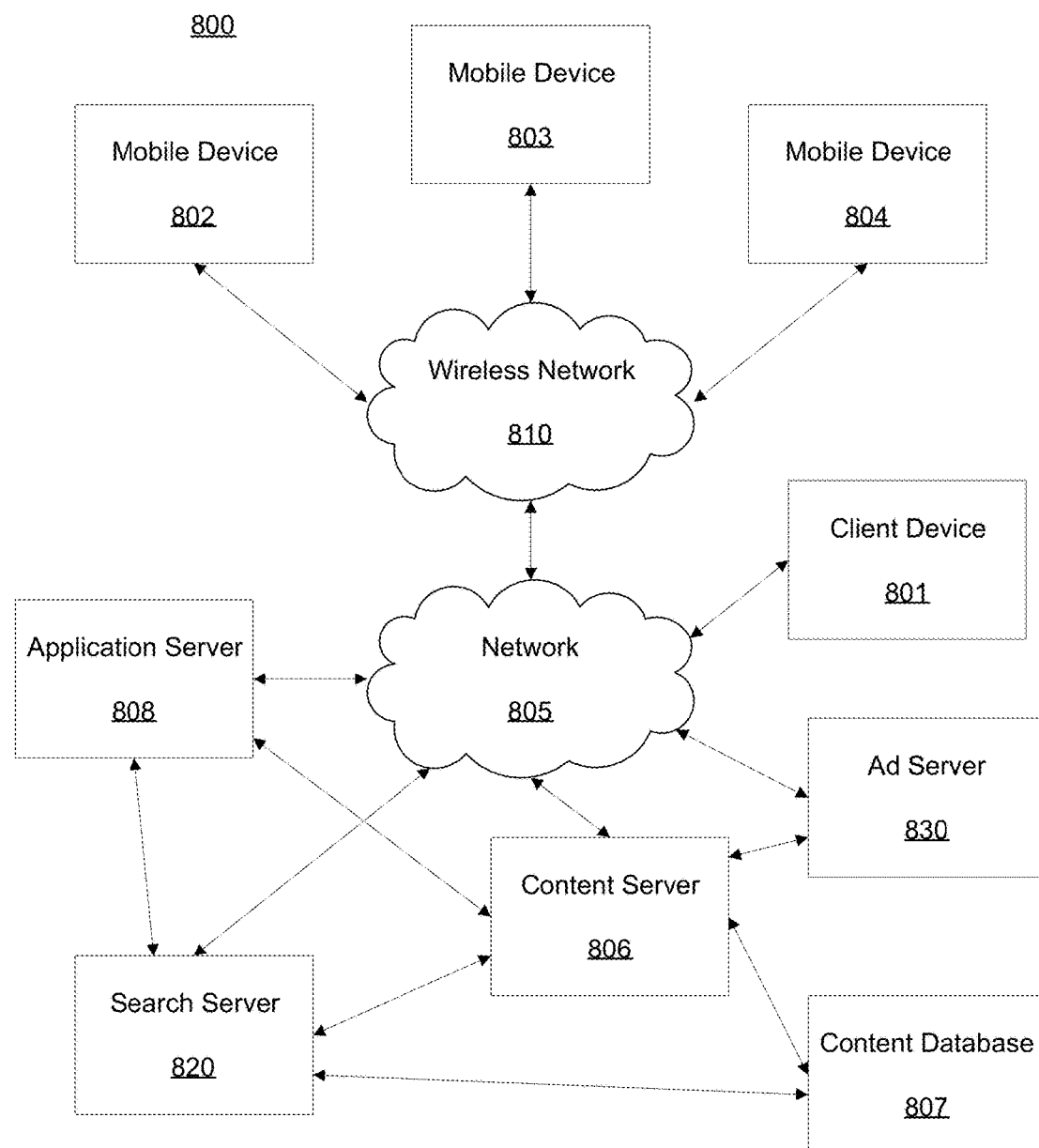
FIG. 8 is a block diagram illustrating mobile devices and a client device in communication with servers according to an embodiment of the present disclosure.

In general, with reference to FIG. 8, a system 800 in accordance with an embodiment of the present disclosure is shown. Not all the components may be required to practice the disclosure, and variations in the arrangement and type of the components may be made without departing from the spirit or scope of the disclosure. As shown, system 800 of FIG. 8 includes local area networks ("LANs")/wide area networks ("WANs")—network 805, wireless network 810, mobile devices (client devices) 802-804 and client device 801. One or more of mobile devices 802-804 and/or client device 801 may be a tag, a smart device, and/or an aggregator. FIG. 8 additionally includes a variety of servers (e.g., central computer), such as content server 806, application (or "App") server 808, search server 820 and advertising ("ad") server 830.

One embodiment of mobile devices 802-804 is described in more detail below. Generally, however, mobile devices 802-804 may include virtually any portable computing device capable of receiving and sending a message over a network, such as network 805, wireless network 810, or the like. Mobile devices 802-804 may also be described generally as client devices that are configured to be portable. Thus, mobile devices 802-804 may include virtually any portable computing device capable of connecting to another computing device and receiving information.

A web-enabled mobile device may include a browser application that is configured to receive and to send web pages, web-based messages, and the like. The browser application may be configured to receive and display graphics, text, multimedia, and the like, employing virtually any web based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message.

Mobile devices 802-804 also may include at least one client application that is configured to receive content from another computing device. The client application may include a capability to provide and receive textual content, graphical content, audio content, and the like. The client application may further provide information that identifies itself, including a type, capability, name, and the like. In one embodiment, mobile devices 802-804 may uniquely identify themselves through any of a variety of mechanisms, including a phone number, Mobile Identification Number (MIN), an electronic serial number (ESN), or other mobile device identifier.

In some embodiments, mobile devices 802-804 may also communicate with non-mobile client devices, such as client device 801, or the like. Client device 801 may include virtually any computing device capable of communicating over a network to send and receive information. The set of such devices may include devices that typically connect using a wired or wireless communications medium such as personal computers, multiprocessor systems, microprocessor-based or programmable consumer electronics, network PCs, or the like. Thus, client device 801 may also have differing capabilities for displaying navigable views of information.

Client devices 801-804 computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like.

Wireless network 810 is configured to couple mobile devices 802-804 and its components with network 805. Wireless network 810 may include any of a variety of wireless sub-networks that may further overlay stand-alone ad-hoc networks, and the like, to provide an infrastructure-oriented connection for mobile devices 802-804. Such sub-networks may include mesh networks, Wireless LAN (WLAN) networks, cellular networks, and the like.

Network 805 is configured to couple content server 806, application server 808, or the like, with other computing devices, including, client device 801, and through wireless network 810 to mobile devices 802-804. Network 805 is enabled to employ any form of computer readable media for communicating information from one electronic device to another. Also, network 805 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another, and/or other computing devices.

Within the communications networks utilized or understood to be applicable to the present disclosure, such networks will employ various protocols that are used for communication over the network. Signal packets communicated via a network, such as a network of participating digital communication networks, may be compatible with or compliant with one or more protocols. Signaling formats or protocols employed may include, for example, TCP/IP, UDP, QUIC (Quick UDP Internet Connection), DECnet, NetBEUI, IPX, APPLETALK™, or the like. Versions of the Internet Protocol (IP) may include IPv4 or IPv6. The Internet refers to a decentralized global network of networks. The Internet includes local area networks (LANs), wide area networks (WANs), wireless networks, or long haul public networks that, for example, allow signal packets to be communicated between LANs. Signal packets may be communicated between nodes of a network, such as, for example, to one or more sites employing a local network address. A signal packet may, for example, be communicated over the Internet from a user site via an access node coupled to the Internet. Likewise, a signal packet may be forwarded via network nodes to a target site coupled to the network via a network access node, for example. A signal packet communicated via the Internet may, for example, be routed via a path of gateways, servers, etc. that may route the signal packet in accordance with a target address and availability of a network path to the target address.

According to some embodiments, the present disclosure may also be utilized within or accessible to an electronic social networking site. A social network refers generally to an electronic network of individuals, such as acquaintances, friends, family, colleagues, or co-workers, that are coupled via a communications network or via a variety of sub-networks. Potentially, additional relationships may subsequently be formed as a result of social interaction via the communications network or sub-networks. In some embodiments, multi-modal communications may occur between members of the social network. Individuals within one or more social networks may interact or communication with other members of a social network via a variety of devices. Multi-modal communication technologies refers to a set of technologies that permit interoperable communication across multiple devices or platforms, such as cell phones, smart phones, tablet computing devices, phablets, personal computers, televisions, set-top boxes, SMS/MMS, email, instant messenger clients, forums, social networking sites, or the like.

In some embodiments, the disclosed networks 810 and/or 805 may comprise a content distribution network(s). A "content delivery network" or "content distribution network" (CDN) generally refers to a distributed content delivery system that comprises a collection of computers or computing devices linked by a network or networks. A CDN may employ software, systems, protocols or techniques to facilitate various services, such as storage, caching, communication of content, or streaming media or applications. A CDN may also enable an entity to operate or manage another's site infrastructure, in whole or in part.

The content server 806 may include a device that includes a configuration to provide content via a network to another device. A content server 806 may, for example, host a site or service, such as streaming media site/service (e.g., Netflix®), an email platform or social networking site, or a personal user site (such as a blog, vlog, online dating site, and the like). A content server 806 may also host a variety of other sites, including, but not limited to business sites, educational sites, dictionary sites, encyclopedia sites, wikis, financial sites, government sites, and the like. Devices that may operate as content server 806 include personal computers desktop computers, multiprocessor systems, microprocessor-based or programmable consumer electronics, network PCs, servers, and the like.

Content server 806 can further provide a variety of services that include, but are not limited to, streaming and/or downloading media services, search services, email services, photo services, web services, social networking services, news services, third-party services, audio services, video services, instant messaging (IM) services, SMS services, MMS services, FTP services, voice over IP (VOIP) services, or the like. Such services, for example a video application and/or video platform, can be provided via the application server 808, whereby a user is able to utilize such service upon the user being authenticated, verified or identified by the service. Examples of content may include images, text, audio, video, or the like, which may be processed in the form of physical signals, such as electrical signals, for example, or may be stored in memory, as physical states, for example.

Moreover, although FIG. 8 illustrates servers 806, 808, 820 and 830 as single computing devices, respectively, the disclosure is not so limited. For example, one or more functions of servers 806, 808, 820 and/or 830 may be distributed across one or more distinct computing devices. Moreover, in one embodiment, servers 806, 808, 820 and/or 830 may be integrated into a single computing device, without departing from the scope of the present disclosure.

Figure 9:
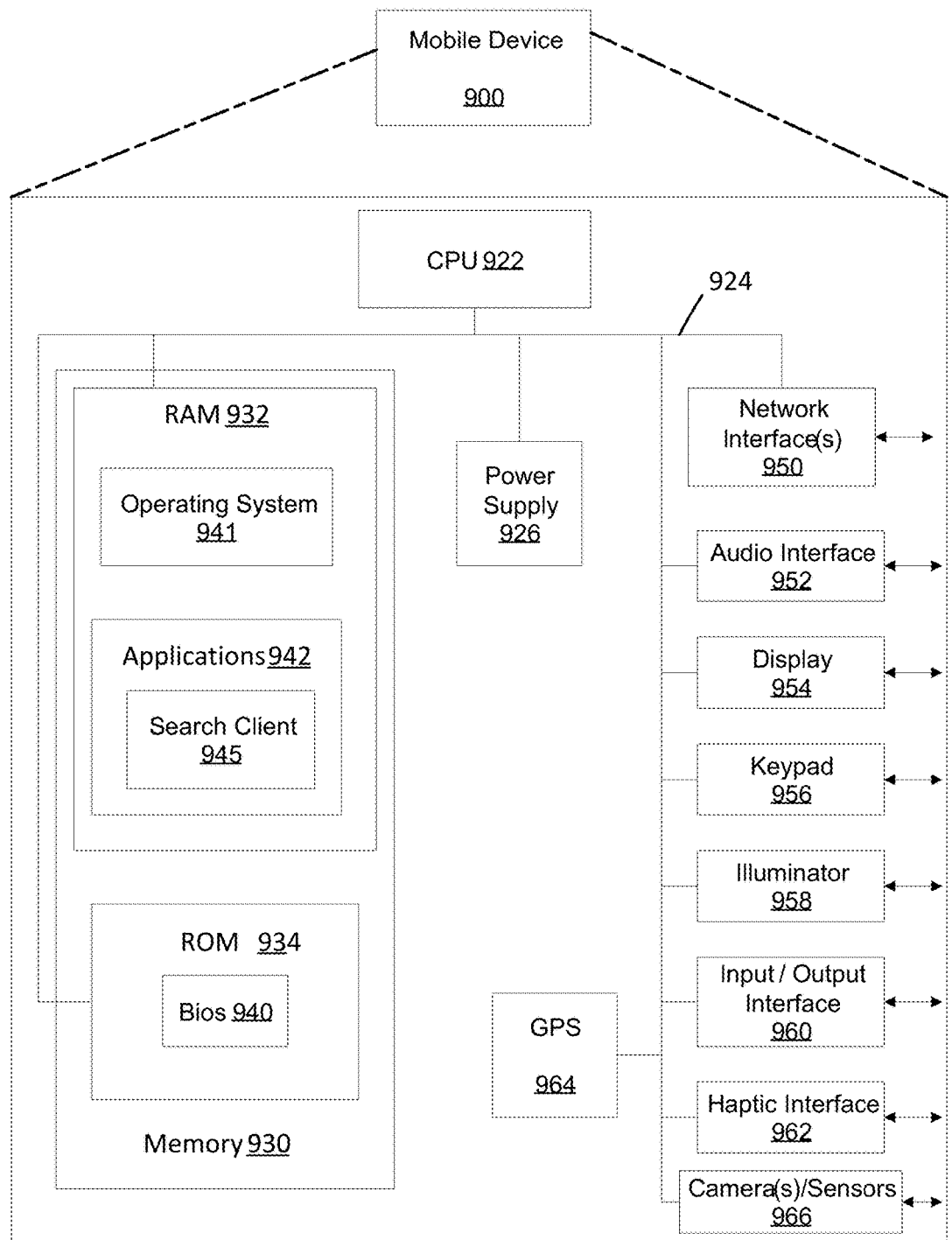
FIG. 9 is a block diagram illustrating components of a mobile device according to an embodiment of the present disclosure.

FIG. 9 is a schematic diagram illustrating a client device showing an example embodiment of a client device that may be used within the present disclosure. Client device 900 may include many more or less components than those shown in FIG. 9. However, the components shown are sufficient to disclose an illustrative embodiment for implementing the present disclosure. Client device 900 may represent, for example, client devices discussed above in relation to FIG. 9.

As shown in the figure, Client device 900 includes a processing unit (CPU) 922 in communication with a mass memory 930 via a bus 924. Client device 900 also includes a power supply 926, one or more network interfaces 950, an audio interface 952, a display 954, a keypad 956, an illuminator 958, an input/output interface 960, a haptic interface 962, an optional global positioning systems (GPS) receiver 964 and a camera(s) or other optical, thermal or electromagnetic sensors 966. Device 900 can include one camera/sensor 966, or a plurality of cameras/sensors 966, as understood by those of skill in the art. The positioning of the camera(s)/sensor(s) 966 on device 900 can change per device 900 model, per device 900 capabilities, and the like, or some combination thereof.

Power supply 926 provides power to Client device 900. A rechargeable or non-rechargeable battery may be used to provide power. The power may also be provided by an external power source, such as an AC adapter or a powered docking cradle that supplements and/or recharges a battery.

Client device 900 may optionally communicate with a base station (not shown), or directly with another computing device. Network interface 950 includes circuitry for coupling Client device 900 to one or more networks, and is constructed for use with one or more communication protocols and technologies as discussed above. Network interface 950 is sometimes known as a transceiver, transceiving device, or network interface card (NIC).

Audio interface 952 is arranged to produce and receive audio signals such as the sound of a human voice. For example, audio interface 952 may be coupled to a speaker and microphone (not shown) to enable telecommunication with others and/or generate an audio acknowledgement for some action. Display 954 may be a liquid crystal display (LCD), gas plasma, light emitting diode (LED), or any other type of display used with a computing device. Display 954 may also include a touch sensitive screen arranged to receive input from an object such as a stylus or a digit from a human hand.

Keypad 956 may comprise any input device arranged to receive input from a user. For example, keypad 956 may include a push button numeric dial, or a keyboard. Keypad 956 may also include command buttons that are associated with selecting and sending images. Illuminator 958 may provide a status indication and/or provide light. Illuminator 958 may remain active for specific periods of time or in response to events. For example, when illuminator 958 is active, it may backlight the buttons on keypad 956 and stay on while the client device is powered. Also, illuminator 958 may backlight these buttons in various patterns when particular actions are performed, such as dialing another client device. Illuminator 958 may also cause light sources positioned within a transparent or translucent case of the client device to illuminate in response to actions.

Client device 900 also comprises input/output interface 960 for communicating with external devices, such as a headset, or other input or output devices not shown in FIG. 9. Input/output interface 960 can utilize one or more communication technologies, such as USB, infrared, Bluetooth™, or the like. Haptic interface 962 is arranged to provide tactile feedback to a user of the client device. For example, the haptic interface may be employed to vibrate client device 900 in a particular way when the Client device 900 receives a communication from another user.

Optional GPS transceiver 964 can determine the physical coordinates of Client device 900 on the surface of the Earth, which typically outputs a location as latitude and longitude values. GPS transceiver 964 can also employ other geo-positioning mechanisms, including, but not limited to, triangulation, assisted GPS (AGPS), E-OTD, CI, SAI, ETA, BSS or the like, to further determine the physical location of Client device 900 on the surface of the Earth. It is understood that under different conditions, GPS transceiver 964 can determine a physical location within millimeters for Client device 900; and in other cases, the determined physical location may be less precise, such as within a meter or significantly greater distances. In one embodiment, however, Client device may through other components, provide other information that may be employed to determine a physical location of the device, including for example, a MAC address, Internet Protocol (IP) address, or the like.

Mass memory 930 includes a RAM 932, a ROM 934, and other storage means. Mass memory 930 illustrates another example of computer storage media for storage of information such as computer readable instructions, data structures, program modules or other data. Mass memory 930 stores a basic input/output system ("BIOS") 940 for controlling low-level operation of Client device 900. The mass memory also stores an operating system 941 for controlling the operation of Client device 900. It will be appreciated that this component may include a general purpose operating system such as a version of UNIX, or LINUX™, or a specialized client communication operating system such as Windows Client™, or the Symbian® operating system. The operating system may include, or interface with a Java virtual machine module that enables control of hardware components and/or operating system operations via Java application programs.

Memory 930 further includes one or more data stores, which can be utilized by Client device 900 to store, among other things, applications 942 and/or other data. For example, data stores may be employed to store information that describes various capabilities of Client device 900. The information may then be provided to another device based on any of a variety of events, including being sent as part of a header during a communication, sent upon request, or the like. At least a portion of the capability information may also be stored on a disk drive or other storage medium (not shown) within Client device 900.

Applications 942 may include computer executable instructions which, when executed by Client device 900, transmit, receive, and/or otherwise process audio, video, images, and enable telecommunication with a server and/or another user of another client device. Other examples of application programs or "apps" in some embodiments include browsers, calendars, contact managers, task managers, transcoders, photo management, database programs, word processing programs, security applications, spreadsheet programs, games, search programs, and so forth. Applications 942 may further include search client 945 that is configured to send, to receive, and/or to otherwise process a search query and/or search result using any known or to be known communication protocols. Although a single search client 945 is illustrated it should be clear that multiple search clients may be employed. For example, one search client may be configured to enter a search query message, where another search client manages search results, and yet another search client is configured to manage serving advertisements, IMs, emails, and other types of known messages, or the like.

Figure 10:
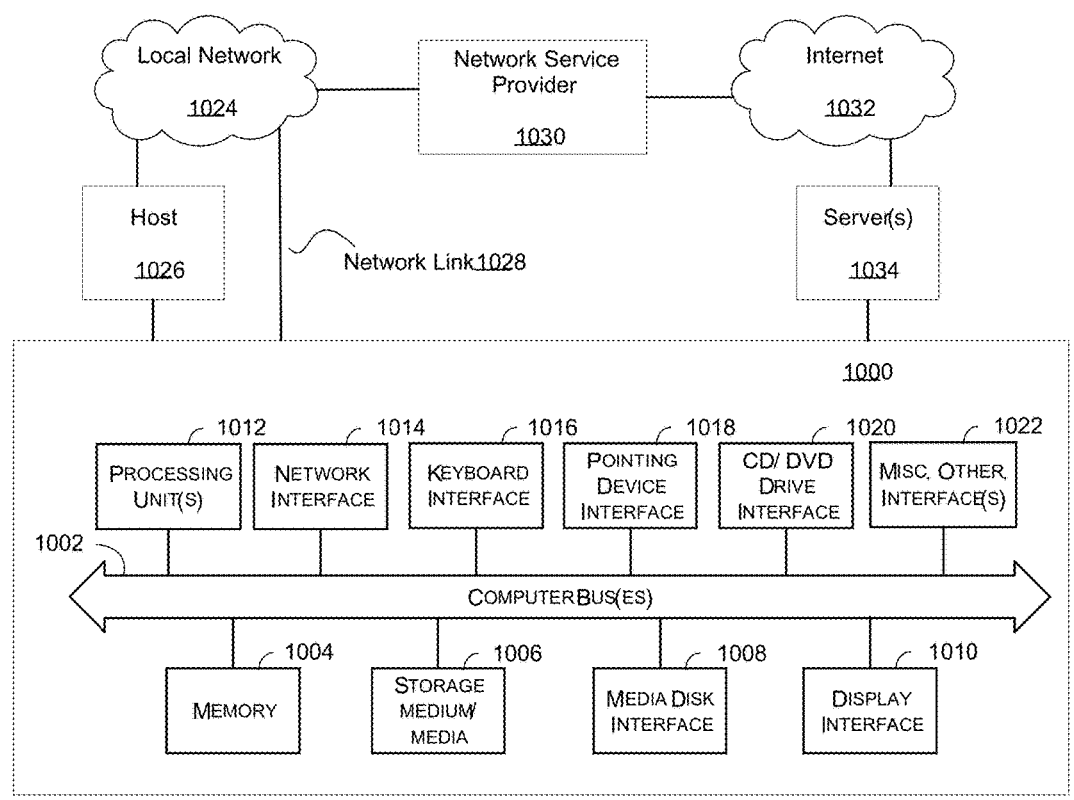
FIG. 10 is a block diagram of an internal architecture of a computing device according to an embodiment of the present disclosure.

As shown in FIG. 10, internal architecture 1000 of a computing device(s), computing system, computing platform and the like can include one or more processing units, processors, or processing cores, (also referred to herein as CPUs) 1012, which interface with at least one computer bus 1002. Also interfacing with computer bus 1002 are, for example, computer-readable medium, or media, 1006, network interface 1014, memory 1004, e.g., random access memory (RAM), run-time transient memory, read only memory (ROM), media disk drive interface 1020 as an interface for a drive that can read and/or write to media including removable media such as floppy, CD-ROM, DVD, media, display interface 1010 as interface for a monitor or other display device, keyboard interface 1016 as interface for a keyboard, pointing device interface 1018 as an interface for a mouse or other pointing device, and miscellaneous other interfaces not shown individually, such as parallel and serial port interfaces and a universal serial bus (USB) interface.

Memory 1004 interfaces with computer bus 1002 so as to provide information stored in memory 1004 to CPU 1012 during execution of software programs such as an operating system, application programs, device drivers, and software modules that comprise program code, and/or computer executable process steps, incorporating functionality described herein, e.g., one or more of process flows described herein. CPU 1012 first loads computer executable process steps from storage, e.g., memory 1004, computer readable storage medium/media 1006, removable media drive, and/or other storage device. CPU 1012 can then execute the stored process steps in order to execute the loaded computer-executable process steps. Stored data, e.g., data stored by a storage device, can be accessed by CPU 1012 during the execution of computer-executable process steps.

Persistent storage, e.g., medium/media 1006, can be used to store an operating system and one or more application programs. Persistent storage can also be used to store device drivers, such as one or more of a digital camera driver, monitor driver, printer driver, scanner driver, or other device drivers, web pages, content files, playlists and other files. Persistent storage can further include program modules and data files used to implement one or more embodiments of the present disclosure.

Network link 1028 typically provides information communication using transmission media through one or more networks to other devices that use or process the information. For example, network link 1028 may provide a connection through local network 1024 to a host computer 1026 or to equipment operated by a Network or Internet Service Provider (ISP) 1030. ISP equipment in turn provides data communication services through the public, worldwide packet-switching communication network of networks now commonly referred to as the Internet 1032.

A computer called a server host 1034 connected to the Internet 1032 hosts a process that provides a service in response to information received over the Internet 1032. For example, server host 1034 hosts a process that provides information representing video data for presentation at display 1010. It is contemplated that the components of system 1000 can be deployed in various configurations within other computer systems, e.g., host and server.

At least some embodiments of the present disclosure are related to the use of computer system 1000 for implementing some or all of the techniques described herein. According to one embodiment, those techniques are performed by computer system 1000 in response to processing unit 1012 executing one or more sequences of one or more processor instructions contained in memory 1004. Such instructions, also called computer instructions, software and program code, may be read into memory 1004 from another computer-readable medium 1006 such as storage device or network link. Execution of the sequences of instructions contained in memory 1004 causes processing unit 1012 to perform one or more of the method steps described herein. In alternative embodiments, hardware, such as ASIC, may be used in place of or in combination with software. Thus, embodiments of the present disclosure are not limited to any specific combination of hardware and software, unless otherwise explicitly stated herein.

The signals transmitted over network link and other networks through communications interface, carry information to and from computer system 1000. Computer system 1000 can send and receive information, including program code, through the networks, among others, through network link and communications interface. In an example using the Internet, a server host transmits program code for a particular application, requested by a message sent from computer, through Internet, ISP equipment, local network and communications interface. The received code may be executed by processor 1002 as it is received, or may be stored in memory 1004 or in storage device or other non-volatile storage for later execution, or both.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

In an embodiment, a method comprises creating, by a plurality of radio emitting devices each comprising a processor and transceiver, a geo-fence within a space, each radio emitting device capable of communicating with neighboring radio emitting devices in the plurality and capable of communicating with aggregators in communication with a central server computer over a network; and determining, by a subset of the plurality of radio emitting devices, a location of a user computing device executing a user application for the space when the user computing device is moved past the geo-fence and into the space, the determined location relative to the subset of the radio emitting devices, each radio emitting device in the subset transitioning from a sleep state to an active state when the user computing device moves within a predetermined distance from the subset of the radio emitting devices.

In an embodiment, a radio emitting device comprises a processor; a transceiver for communicating with other radio emitting devices and for communicating with an aggregator in communication with a central server computer over a network; and a storage medium for tangibly storing thereon program logic for execution by the processor, the program logic comprising radio emitting device communicating logic executed by the processor for communicating with a plurality of radio emitting devices to create a geo-fence within a space and for facilitating determination of a location of a user computing device by the radio emitting device and a subset of the plurality of radio emitting devices, the user computing device executing a user application for the space, the facilitating determination of the location occurring when the user computing device is moved past the geo-fence and into the space, the determined location relative to the radio emitting device, the radio emitting device transitioning from a sleep state to an active state when the user computing device moves within a predetermined distance from the subset of the radio emitting devices.

In an embodiment, a non-transitory computer readable storage medium tangibly storing thereon computer instructions for execution by a processor of a radio emitting device, the computer instructions comprising communicating with a plurality of radio emitting devices to create a geo-fence within a space and for facilitating determination of a location of a user computing device by the radio emitting device and a subset of the plurality of radio emitting devices, the user computing device executing a user application for the space, the facilitating determination of the location occurring when the user computing device is moved past the geo-fence and into the space, the determined location relative to the radio emitting device, the radio emitting device transitioning from a sleep state to an active state when the user computing device moves within a predetermined distance from the subset of the radio emitting devices.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure. All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A method comprising:

creating, by communication between a plurality of radio emitting devices in a meshed network with each radio emitting device comprising a processor and transceiver, a geo-fence within a space, each radio emitting device capable of communicating with neighboring radio emitting devices in the plurality and capable of communicating with aggregators in communication with a central server computer over a network; and determining, by a subset of the plurality of radio emitting devices, a location of a user computing device executing a user application for the space when the user computing device is moved past the geo-fence and into the space, the determined location relative to the subset of the radio emitting devices, each radio emitting device in the subset transitioning from a sleep state to an active state based on wireless transmissions from the subset of radio emitting devices when the user computing device moves within a predetermined distance from the subset of the radio emitting devices.

2. The method of claim 1, further comprising providing a tag cloud comprising the plurality of radio emitting devices.

3. The method of claim 1, wherein the user application provides product information about a product to the user computing device.

4. The method of claim 3, wherein the product information is provided when the user computing device moves within a predetermined distance from the product.

5. The method of claim 3, wherein the product information comprises navigation information to the product.

6. The method of claim 1, wherein the user application provides environment information within the space to the user computing device.

7. The method of claim 1, wherein the active state of the radio emitting device comprises increasing transmitting power and transmitting frequency levels.

8. The method of claim 1, wherein the sleep state of the radio emitting device comprises decreasing transmitting power and transmitting frequency levels.

9. The method of claim 1, wherein the user application automatically checks a user of the user computing device into the space when the user computing device moves past the geo-fence.

10. A radio emitting device comprising:
- a processor;
- a transceiver for communicating with other radio emitting devices and for communicating with an aggregator in communication with a central server computer over a network; and
- a non-transitory storage medium for tangibly storing thereon program logic for execution by the processor, the program logic comprising:
- radio emitting device communicating logic executed by the processor for communicating with a plurality of radio emitting devices in a meshed network to create a geo-fence within a space and for facilitating determination of a location of a user computing device by the radio emitting device and a subset of the plurality of radio emitting devices, the user computing device executing a user application for the space, the facilitating determination of the location occurring when the user computing device is moved past the geo-fence and into the space, the determined location relative to the radio emitting device, the radio emitting device transitioning from a sleep state to an active state based on wireless transmissions from the subset of radio emitting devices when the user computing device moves within a predetermined distance from the subset of the radio emitting devices.

11. The radio emitting device of claim 10, wherein the user application provides product information about a product to the user computing device.

12. The radio emitting device of claim 11, wherein the product information is provided when the user computing device moves within a predetermined distance from the product.

13. The radio emitting device of claim 11, wherein the product information comprises navigation information to the product.

14. The radio emitting device of claim 10, wherein the user application provides environment information within the space to the user computing device.

15. The radio emitting device of claim 10, further comprising increasing transmitting power and transmitting frequency levels when in the active state.

16. The radio emitting device of claim 10, further comprising decreasing transmitting power and transmitting frequency levels when in the sleep state.

17. The radio emitting device of claim 10, wherein the user application automatically checks a user of the user computing device into the space when the user computing device moves past the geo-fence.

18. A non-transitory computer readable storage medium tangibly storing thereon computer instructions for execution by a processor of a radio emitting device, the computer instructions comprising:
- communicating with a plurality of radio emitting devices in a meshed network to create a geo-fence within a space and for facilitating determination of a location of a user computing device by the radio emitting device and a subset of the plurality of radio emitting devices, the user computing device executing a user application for the space, the facilitating determination of the location occurring when the user computing device is moved past the geo-fence and into the space, the determined location relative to the radio emitting device, the radio emitting device transitioning from a sleep state to an active state based on wireless transmissions from the subset of radio emitting devices when the user computing device moves within a predetermined distance from the subset of the radio emitting devices.

19. The medium of claim 18, wherein the user application provides product information about a product to the user computing device.

20. The medium of claim 18, wherein the user application automatically checks a user of the user computing device into the space when the user computing device moves past the geo-fence.

* * * * *